(12) United States Patent
Moore et al.

(10) Patent No.: US 10,215,875 B2
(45) Date of Patent: Feb. 26, 2019

(54) METAL DETECTOR

(71) Applicant: ILLINOIS TOOL WORKS INC., Glenview, IL (US)

(72) Inventors: John Colin Moore, Hampshire (GB); Colin Michael Tagg, Surrey (GB)

(73) Assignee: ILLINOIS TOOL WORKS INC., Glenview, IL (US)

( * ) Notice: Subject to any disclaimer, the term of this patent is extended or adjusted under 35 U.S.C. 154(b) by 860 days.

(21) Appl. No.: 14/377,522

(22) PCT Filed: Feb. 7, 2013

(86) PCT No.: PCT/US2013/025040
§ 371 (c)(1),
(2) Date: Aug. 8, 2014

(87) PCT Pub. No.: WO2013/119741
PCT Pub. Date: Aug. 15, 2013

(65) Prior Publication Data
US 2015/0234075 A1     Aug. 20, 2015

(30) Foreign Application Priority Data
Feb. 10, 2012  (GB) .................................. 1202324.8
Oct. 15, 2012  (GB) .................................. 1218448.7

(51) Int. Cl.
*G01V 3/10*     (2006.01)
*G01N 27/90*    (2006.01)

(52) U.S. Cl.
CPC ........... *G01V 3/10* (2013.01); *G01N 27/9033* (2013.01)

(58) Field of Classification Search
CPC ......... G01J 5/16; G01K 7/10; G01L 19/0092; G01R 11/18; G01R 11/185; G01R 11/19; G01R 19/32; G01R 21/14; G01R 33/0082
See application file for complete search history.

(56) References Cited

U.S. PATENT DOCUMENTS

| 4,563,645 A | 1/1986 | Kerr |
| 5,189,366 A | 2/1993 | Mayo |

(Continued)

FOREIGN PATENT DOCUMENTS

| CN | 1582385 A | 2/2005 |
| CN | 1705862 A | 12/2005 |

(Continued)

OTHER PUBLICATIONS

ISR and WO for PCT/US2013/025040 dated Jul. 16, 2013.

*Primary Examiner* — Tung X Nguyen
(74) *Attorney, Agent, or Firm* — Thompson Hine LLP

(57) ABSTRACT

A method of operation of a variable frequency metal detector having a driver circuit for establishing an alternating magnetic field in a coil system so as to generate an output signal at a given frequency, said driver circuit comprises a plurality of switches being arranged to cause the coil system to be driven at a frequency determined by the operation of the plurality switches, the method comprising the steps of generating an adjustable balance signal, combining the adjustable balance signal with the output signal of the detector, and varying the adjustable balance signal so as to provide a compensated signal whereby the output signal and/or the adjustable balance signal is filtered to remove one or more harmonics.

54 Claims, 14 Drawing Sheets

(56) References Cited

U.S. PATENT DOCUMENTS

| | | | |
|---|---|---|---|
| 5,691,640 A | 11/1997 | King | |
| 5,729,143 A | 3/1998 | Tavernetti | |
| 7,474,102 B2 * | 1/2009 | Candy | G01V 3/104 |
| | | | 324/228 |
| 8,278,918 B2 * | 10/2012 | McAdam | G01V 3/107 |
| | | | 324/228 |
| 8,473,235 B2 | 6/2013 | Kittel et al. | |
| 2005/0030010 A1 | 2/2005 | Jones et al. | |
| 2006/0119351 A1 | 6/2006 | James et al. | |
| 2007/0007953 A1 | 1/2007 | Keene et al. | |
| 2009/0318098 A1 * | 12/2009 | Stamatescu | G01V 3/104 |
| | | | 455/118 |

FOREIGN PATENT DOCUMENTS

| | | | |
|---|---|---|---|
| EP | 1663529 | B1 | 6/2006 |
| GB | 2361544 | B | 10/2001 |
| GB | 2423366 | A | 8/2006 |
| JP | H0792274 | A | 4/1995 |
| JP | H09304352 | A | 11/1997 |
| WO | 88/03273 | A1 | 5/1988 |
| WO | 02/25318 | A1 | 3/2002 |
| WO | 2006/087510 | A1 | 8/2006 |
| WO | WO2012045578 | A1 | 4/2012 |

\* cited by examiner

METAL DETECTOR

RELATED APPLICATIONS

The present application is a National Phase of International Application Number PCT/US2013/025040 filed Feb. 7, 2013 and claims priority of United Kingdom Application Number 1202324.8, filed Feb. 10, 2012 and United Kingdom Application Number 1218448.7 filed Oct. 15, 2012.

FIELD OF INVENTION

The present invention relates to an apparatus for detecting contaminants. More particularly but not exclusively the present invention relates to an apparatus for detecting metal in foodstuffs.

INTRODUCTION

Foreign bodies in their products are one of the biggest sources of customer complaints for many food manufacturers and retailers. Such foreign bodies can be any undesirable solid objects and include items entirely unconnected with the food such as glass or metal fragments, as well as those related to the food such as bones. One of the biggest concerns for the food processing industry is the unwanted inclusion of metallic particles or metallic items in the food product as a result of processing. For example, typical metal inclusions range from nuts or washers lost from the processing machinery or dropped during maintenance etc, to metal shavings, e.g. produced by mechanical wear.

Such metal inclusions will not only compromise product safety and raise health concerns but also have a negative impact on the food manufacturer's and ultimately the retailer's reputation. Legislation has demanded that food manufacturing industries should provide effective measures to prevent the presence of foreign bodies in the food product. Compliance with this requirement may be accomplished by using sieves, traps or more sophisticated techniques such as metal detectors. Due to the risk of damage to their reputation, more stringent quality control measures now expected by most food retailers are forcing food manufactures to use more up to date metal detection techniques.

Apparatus for detecting metal contaminants in food products is well known in the industry and is described in WO 02/25318 (Safeline Limited) and WO2006/087510 (Spectrum Inspection Systems Limited). A typical metal detector shown in FIG. 1 of WO2006/087510 (Spectrum Inspection Systems Limited) consists of a screened search head with an aperture through which the product passes and a control unit which processes the signals from the head. Inside the head there is a three coil system surrounding the aperture. A transmitter coil surrounding the aperture with its axis arranged parallel to the conveying direction is connected to a high frequency generating circuit. Above and below the aperture are receiver or detection coils with their axes arranged vertically. The two receiver coils are identical and are placed the same distance from the transmitter coil, so that in the absence of any disturbance of the varying magnetic field inside the search head, they receive the same signal and produce an identical output voltage. The receiver coils are connected in opposition such that in absence of any object their induced voltages oppose one another and thereby cancel each other out resulting in a zero output signal. This is the condition when the coil system is in a perfectly balanced state.

When an electrically conductive particle passes through the coils of the metal detector, the high frequency field is disrupted through one of the receiver coils due to induced currents in the particle's surface which causes slight changes in the balance condition, e.g. by a few microvolts, resulting in the output from the coils no longer being zero. Suitable amplification and processing is used to trigger an automatic reject alarm. The ease of detection will depend on the magnetic permeability and electrical conductivity of the product to be tested as well as the field frequency and the size, electrical resistance and magnetic permeability of the contaminant. The signals created by various metals as they pass through the coils of a metal detector can be split into two components: resistive and reactive, according to the conductivity and magnetic permeability of the metal, the reactive component being substantially 90° out of phase with respect to the resistive component as shown in the vector diagram in FIG. 1. With reference to FIG. 1, a non-ferrous but conductive material, such as copper or stainless steel, will generate an output signal, $V_{S1}$ having largely a 'resistive' component and therefore, is generally in phase with the drive signal, $V_D$. Due to losses in the material, the component of the output signal $V_{S2}$ from a poor conductor such as a ferrite material will substantially be in phase quadrature to the resistive component of the signal. For most materials such as ferrous materials which contain iron that exhibit some magnetic effect and some electrical conductivity would generate an output signal having a resistive component and a reactive component. With reference to FIG. 1, the vector line from a ferrous material would therefore lie between the reactive and resistive component. This is fundamental to the operation of a metal detector and such a device is capable of detecting particles of different metal types.

Typically a metal particle may create as little as 1 in 10 million disturbance in the magnetic field. Since the size, shape and orientation of metal contaminants is impossible to control, the metal detector is usually set at the highest possible sensitivity setting. However, the adverse effect of this is that moist food such as cheese, fresh meat, warm bread, jam, pickles etc., although only very slightly conductive, due to their large size, e.g. a whole chicken, the effect at a particular frequency is more noticeable by the detection coils. Without any form of discrimination, the detection of the food will be treated as a contaminant even though metal is not present. In some cases the signal from the product can be many times larger than that of a small metallic contaminant to be detected. This is known as the "product effect" and is due to the product itself exhibiting slight electrical conductivity, e.g. when moist and salty. This can be represented graphically in FIG. 1 and the signal from a non-magnetic and weakly conductive material is represented by the vector $V_{S3}$. The length of the arrow represents the magnitude of the signal and the direction represents the phase of the signal. A chicken passing through the detector will generate a large output signal which will vary in magnitude as the chicken passes through the detector, simply because of the varying volume of chicken affecting the field. However, the phase of the signal will be constant because the conductive properties will be substantially the same throughout the chicken. For example, this is represented in FIG. 1 with the signal being 110° out of phase with the drive signal, due to vector $V_{S3}$ comprising largely of a resistive component but also having a small component due to the slightly conductive nature of the chicken.

In order to cancel out interference from moist foods, WO 2006/087510 (Spectrum Inspection Systems Limited)

describes tuning the metal detector to favour signals in a given phase whilst discriminating or ignoring signals 90° to this direction. A reference signal Vref based on the drive or transmitter signal is generated whereby its phase is adjusted so that it is in phase quadrature (90°) with the output signal $V_{S3}$ for a non-contaminated food product. $V_{ref}$ and $V_{S3}$ are then compared by a phase sensitive detector which will provide an output signal that will discriminate signals from the non-contaminated food product, $V_{S3}$, i.e. provide a substantially zero output signal (signals in phase quadrature provide a zero output from a phase discriminator since the cosine of the phase angle between both signals is zero). In this way, unwanted product signals may be tuned out or discriminated from signals produced by metallic contaminants by varying the reference signal applied to the phase detectors. Thus the system is able to detect metals or other contaminants having magnetic or conductive properties, where the phase of the component of the output signal associated with the contaminant occurs at a substantially different phase angle to that of the component associated with the product.

In the case where a food product has a metal or other conductive or ferromagnetic particle embedded in it, either of a magnetic material or a conductive material, then the output signal will comprise an additional component $V_{S8}$ associated with the disturbance of the magnetic field caused by the presence of the metal particle. Although the amplitude of the component $V_{S8}$ of the output signal will be small compared to the signal $V_{S3}$ from the product, the signal $V_{S8}$ will not normally be in phase quadrature with the reference signal $V_{ref}$. Thus, the resultant component $V_m$ will not be ignored by the phase sensitive detector resulting in an increase in the output signal from the phase sensitive detector (see FIG. 2). This can be supplied to a level detector which triggers an alarm when a predetermined threshold is reached.

The above system works well for detecting metals having magnetic or conductive properties, where the phase of the component of the output signal associated with the metal occurs at a substantially different angle to that of the component associated with the product. However, in the case of stainless steel, the phase of the output signal generated may substantially correspond to the output signal from the product at a given frequency. Thus, the components of the output signal generated by the metal particle will be in phase quadrature with the reference signal and will not be detected by the phase sensitive detector. As the magnitude and phase of the output signal depends largely on the frequency of the drive signal and the size of the stainless steel particle, then one would naturally vary the frequency of the drive signal so that the phase component of the output signal associated with that metal particle will be out of phase with the component of the output signal associated with the product. However, the choice of available frequencies is limited when the driving coil is driven by a tuned circuit. To overcome the limited selection of frequencies offered by a known tuned circuit, WO 2006/087510 (Spectrum Inspection Systems Limited) teaches a variable frequency metal detector in which the signal in the drive coil is driven at selected frequencies by means of a plurality of switches. This allows the signal in the drive coil to be driven at a greater range of frequencies than with a tuned circuit.

Despite the detection coils being set in a near perfectly balanced state at the factory site or by means of being commissioned by a technical person at the customer's site, there will still be occasions where the detection coil system will fail to be in a balanced state with no test items or contaminants present, resulting in perfectly acceptable food products being rejected. For example, the balance of the detector can be disturbed due to transport or movement of the detector or other structural changes resulting in movement of the coils. Also, metal or magnetically susceptible objects may come into the vicinity of the magnetic field of the detection coils causing disruption in the magnetic field of the detection coil system, generating a false output signal.

In the case where the sensitivity of the metal detector is set very high so as to detect very small disturbances in magnetic field associated with small metal particles, under certain circumstances an out of balance in the detection coils can have a profound effect on the operation of the detection circuitry such as the detection coil amplifiers and phase sensitive detectors, which only operate over a limited voltage signal range. When the detection coils are in an imbalanced state there is a greater likelihood that the output signal from moist products as a result of the "product effect" will saturate the detection circuitry at a given operational frequency. For example, this can be illustrated in FIG. 3 with reference to a sinusoidal wave 8 having a peak-to-peak value in excess of the saturation limit of +/−12v of the detection circuitry. In an ideal situation, the output signal should read zero if the system is in a perfectly balanced state or below a predetermined threshold value. However, when the detection coil system is in a largely imbalanced state to the extent that the output signal 10 occupies a significant portion of the operational range of the detection circuitry, any additional disturbance in the magnetic field as a result of the product effect would greatly increase the output signal beyond the saturation limit of the detection circuitry. This is schematically demonstrated in FIG. 3 showing the tops 14 (shown as dashed lines) of the output signal being "lost". To bring the output signal into range, the drive signal is turned down, thereby reducing the strength of the magnetic field between the detection coils but this is at the expense of reduced sensitivity of the metal detector. Thus, there is the risk that metal particles, particularly small metal particles would to be undetected as the disturbance in the magnetic field to be picked up by the detection circuitry would only be very slight. Moreover, the saturation of the detection circuitry may result in the detector not recognising a component of the output signal associated with a particular metal contaminant being out of phase with the component of the output signal associated with the product and therefore, likely to be ignored as discussed above.

In an attempt to mitigate such detection inaccuracies, the detection coil is re-balanced at each given operational frequency of the detector so bringing the balance signal closer to the zero line and thereby reducing the possibility that the detection circuitry would saturate. With reference to FIG. 3, this has the effect of increasing the "headroom" signal 16 representing the distance from the peak of the balance signal to the saturation limit of the detection circuitry for detection purposes. Typically a mechanical balance is employed to balance the detection coils. FIG. 4 shows a schematic arrangement of the coil configuration 18 embodying a mechanical balance 20 in the form of a coil or loop connected between the receiver coils, 22 and 24. The receiver coils 22, 24 are shown connected in series. The mechanical balance 20 provides some slack to the receiver coils 22 and 24 in order to enable their effective distance from the transmitter coil 26 to be adjusted which in turn causes changes to their magnetic field. One of the criteria for balancing the coil system 18 is that the effective distance of each of the receiver coils 22 and 24 from the transmitter coil 26 is identical. Since the physical properties of the receiver coils such as the shape, size and the number of windings are identical, by varying the relative distances from one another of the coil within the system 18, the output signal can be finely adjusted. The detector is balanced by manually manipulating the mechanical balance 20 usually by hand or a specialist tool to cause the effective distance of one of the receiver coils 22 and/or 24 to be adjusted. Once adjusted, the mechanical balance 20 is then encapsulated in a resin to prevent any further movement through physical shocks or handling of the metal detector. The mechanical balance 20 shown in FIG. 4 provides fine adjustments to the balance at a given frequency. For crude adjustments to the balance and in combination or separate to the loop or coil 20, an alternative mechanical balance can be provided. This involves placing a block of metal of a predetermined size in the vicinity of the coil system to cause deliberate interference in the magnetic field. By adjusting the position of the metal block between or around the receiver coils 22 and 24, the balance of the detection coil system can thereby be adjusted. Even though the mechanical balance once calibrated is thereafter encapsulated in resin to prevent any further movement, the method of calibration is prone to error. Any slight movement of the mechanical balance out of balance during the setting of the resin, would mean that the resin or seal has to be broken again and re-done. Moreover, this balancing technique only provides balancing of the coils at one frequency. To balance the detection coils at the other frequencies, would mean repeatedly manipulating the detection coils to cater for the other frequencies.

In contrast to a tuned circuit, modern metal detectors, as that taught in WO 2006/087510 (Spectrum Inspection Systems Ltd), operate over a large range of frequencies, e.g. 40 kHz to 900 kHz. The time, effort and expense to re-set the balance mechanically at each successive frequency can sometimes be excessive and in some cases the result is not very accurate. Moreover, in a majority of cases the mechanical balance is permanently set in resin, making it impossible to re-set the balance mechanically. As a result only a few select frequencies are chosen for balancing, e.g. usually one at each extremity of the frequency range and one in the middle. FIG. 5 shows an exemplified distribution of the output signal 10 of a metal detector throughout the operational frequency range of the detector with no product to be tested or contaminant present. Although, the detection coils are effectively balanced at the selected frequencies, A, B and C (see FIG. 5), this is not the case of the output signal 10 from the detection coils outside of the selected frequencies resulting in a non-zero output signal. Thus, where a frequency is used for the detection of a particular metal type that falls outside of the selected frequencies, A, B and C there is a risk that the detection circuitry will saturate with consequential effects as discussed above.

WO 02/25318 (Safeline Limited) touches upon an automatic balance technique whereby, when the coils are out of balance, the out of balance signal determined by a digital signal processor causes a synthesiser to generate a corrective signal for subtraction from the coil output signal to cancel out the balance signal. No further detail is provided how this is achieved since it is necessary that phase and magnitude of the outbalance signal is correctly determined each time the output signal is out of balance in order to provide the necessary corrective signal. More importantly, the automatic balance only caters for signals of a sinusoidal nature derived from a tuned circuit and therefore, not geared for variable frequency metal detectors as taught in WO 2006/087510 (Spectrum Inspection Systems Limited).

As discussed above with reference to the vector diagram shown in FIG. 1, the detection coil system produces two signals, known as the resistive and reactive signals, which tell the detector about the interaction of the product with the magnetic field. Conductive products such as copper or stainless will generate an output signal having largely a resistive component. On the other hand, due to losses in the material, the component of the output signal from a poor conductor but perfect or near perfect magnetic material will substantially be in phase quadrature with the resistive signal. The differing output signals from the receiver coils will vary depending upon how conductive the product is. For instance, different types of products will interact differently with the magnetic field, each product having a resistive component and a reactive component and therefore, a characteristic phase angle.

When a perfectly magnetic material is passed between the receiver coils, one would expect a relatively weak or no resistive component indicating a weak conductive material component and a strong reactive component indicating a strong magnetic material. In reality, this is not exactly the case and a perfectly magnetic material exhibits both a reactive component and a notable resistive component resulting in a slight shift in phase angle from the drive signal. This shift in phase angle can be attributed to the delay in monitoring or recording or processing the output signal from the receiver coils. During the interaction of the product with the magnetic field between the receiver coils, there is a slight delay in the system picking up the signal. In circumstances where the product is a dry product (no electrical conductivity), such as a hard frozen product, a small phase angle is generated. This delay could be due to the interaction of the changing magnetic field with the receiver coils and the subsequent detection of the signal in the receiver coils as a result of the electronics in the detectors (e.g. phase sensitive detectors). This delay is usually characteristic of a particular metal detector and is traditionally calibrated by tuning the metal detector to compensate out or discriminate signals representing the resistive component and favouring signals 90° to this signal representing the reactive component in the presence of a ferrite wand between the detection coils Without compensating for this delay in the output signal, products such as dry products which exhibit little or no electrical conductivity may result in a notable signal being detected by the detection circuitry.

For a simple metal detector whereby the drive coil is driven by a tuning circuit operating over a limited range of frequencies, to calibrate for this delay and noise, the ferrite wand is passed between the detection coils at a given operating frequency, and the generated output signal is noted. Any discrepancy in the output signal, as a result of the interaction of the magnetic field with the ferrite, appropriate capacitors are then added to the tuning circuit to discriminate the output signal in the resistive phase. The time and effort to manually add capacitors to the tuning circuit to compensate for this delay factor, can be cumbersome and is prone to mistakes. Moreover, the whole manual correction of this delay would need to be repeated at the different operating frequencies. In the case of a variable frequency metal detector operating over a large range of frequencies, a lot of time and effort would be needed to calibrate for this delay factor at every operating frequency.

Moreover, the detection coils are very sensitive such that a signal is generated from any external influence such as a slight movement or vibration of the coils or the presence of any foreign metallic objects nearby the coils resulting in an undesirable noise being generated from the detection coils.

When calibrating the metal detector for dry products (no electrical conductivity), such as hard frozen products (around −18° C.), without any form of calibration of this noise, the metal detector will be confused as to whether the noise is responsible of the interaction of the dry product with the magnetic field or whether it's just background noise. To compensate for this noise, a ferrite wand is passed between the detection coils as it produces a signal that closely resembles moving metal, i.e. similar to the noise signal. By compensating out or discriminating signals from a ferrite wand, the metal detector becomes very stable to vibrational noises. As the nature of the noise varies with frequency, to compensate for this noise at the different operational frequencies of the metal detector necessitates manually tuning the tuning circuit by adding appropriate capacitors at the different operating frequencies so as to discriminate signals from a ferrite wand.

A system is thus required that:—
a) automatically balances the detector coil system throughout a range of operational frequencies irrespective of the shape of the signal, e.g. whether sinusoidal or not, so as to account for any imbalance in the detector coil system without the need to mechanically adjust the coils, and which ensures an adequately small or zero output signal in the absence of product and/or contaminants across a wide frequency range;
b) automatically compensates for any delays or noise as a result of external influences in measuring the output signal without any or minimal manual intervention.

SUMMARY OF INVENTION

The present applicant has mitigated the above problems by providing an adjustable balance signal to counteract any imbalance in the coil system. More particularly, the present applicant provides a method of operation of a variable frequency metal detector having a driver circuit for establishing an alternating magnetic field in the coil system so as to generate an output signal at a given frequency; said driver circuit comprises a plurality of switches being arranged to cause the coil system to be driven at a frequency determined by the operation of the plurality switches, the method comprising the steps of:—
a. generating an adjustable balance signal;
b. combining the adjustable balance signal with the output of the detector.
c. adjusting the adjustable balance signal so as to provide a compensated signal whereby the output signal and/or the adjustable balance signal is filtered to remove one or more harmonics.

Generating an adjustable balance signal to combine with the output signal of the detector coil system, enables any imbalance in the system to be counteracted. Any signal generating device (driver) can be used to generate and vary an adjustable balance signal. Examples, include a digital oscillator, a synthesiser, an Electronic Programmable Logic Device (EPLD) or even a signal derived from the clock speed of a Central processing Unit. More particularly, the adjustable balance signal can be varied to an extent so that when combined with the output of the detector it nullifies the output signal. The adjustable balance signal is injected or bled from a drive signal used to drive the drive coil (drive signal) to combine with the output signal. Preferably, the driver circuit generates a drive signal for establishing an alternating magnetic field in the coil system and the adjustable balance signal is derived from the drive signal. For example, the signal to drive the drive coil can be based on an internal clock oscillator of the EPLD which is used to generate a varying signal of a given frequency to control a plurality of switches, e.g. Field Effect Transistors (FET) in a driver circuit as taught in WO 2006/087510 (Spectrum Inspection Systems Limited). Typically, an EPLD comprises one or more drive maps stored in the EPLD, a CPU coupled to the EPLD selects a drive map which then controls the internal clock oscillator to send appropriate signals to a driver to repeatedly control the operation of a plurality of switches to generate a signal of a given frequency. Alternatively, the drive maps for driving the EPLD can equally be stored in the CPU. As the adjustable balance signal is derived from the drive signal, the adjustable balance signal will be at the same frequency as the drive signal but with a fixed phase relationship. In terms of the total output signal, by nullifying any imbalance in the output signal and in absence of any products between the coil system or for 'dry products', i.e. products that do not generate a signal in the coil system, reserves a greater portion of the output signal or "headroom" signal for detection of contaminants without saturating the detection coil amplifiers. Ideally maximum range or "headroom" signal for the detection of contaminants is provided by effectively nullifying any imbalance in the coil system. This in turn permits the drive signal to be "turned-up" (i.e. increase the voltage supplied to the drive coil) so increasing the sensitivity of the metal detector to detect small variances in the output signal without saturating the detection circuitry.

Preferably, the compensated signal is measured and if the compensated signal is above a predetermined threshold value, repeat step (c) above so that when combined with the output signal of the detector, the compensated signal is below a predetermined threshold value. Preferably, the predetermined threshold value is equal to substantially zero for a perfectly balanced system but can be any value chosen so as to give a balanced coil system, e.g. sufficiently balanced for useful contaminant detection. Typically, a metal detector has a detection range beyond which the metal detector, more particularly the detection circuitry, will saturate. Ideally, the predetermined threshold value is less than substantially 40% of the detection range of the detection circuitry, preferably less than substantially 15% of the detection range of the detection circuitry, more preferably less than substantially 10% of the detection range of the detection circuitry. Thus for a given frequency, where there is an imbalance in the coil system resulting in a non-zero output signal or outside the permitted range in the absence of any product or contaminant or for dry products, the system automatically varies the adjustable balance signal so that the adjustable balance signal combines with the output of the detector to compensate for this non-zero output to bring it into balance, e.g. resulting in a substantially zero signal or below a predetermined threshold value. This could be done through a trial and error process, e.g. varying the adjustable balance signal incrementally and for each incremental step, the output signal is measured to see if it is below a permitted range. Once the output signal is below a permitted range, the adjustment made to the adjustable balance signal is stored. For example, a detection circuitry operating at a peak-to-peak detection range of +/−12 volts, then the permitted predetermined threshold value to establish balancing of the metal detector in the absence of products in the detection coils would result in an output voltage of less than substantially 4.8 volts, preferably less than substantially 1.8 volts, more preferably less than substantially 1.2 volts.

Optionally, the adjustable balance signal at a given frequency is combined with the output of the detector coil system by superimposing the adjustable balance signal on the output signal. More preferably, the method of compensating the output signal with the adjustable balance signal can involve calculating the difference between the adjustable balance signal and the output signal, e.g. magnitude and phase. To balance the coil system, the phase and amplitude of the adjustable balance signal are varied so that when subtracted from the output signal substantially nullifies the output signal. This can be represented graphically by the vector diagram in FIG. 1. An imbalance in the output signal is shown by the vector $V_{out}$ having a phase component and an amplitude determined by the length of the vector. To nullify the output signal, $V_{out}$, the adjustable balance signal $V_{ABS}$ is varied so that its phase component and amplitude are substantially equal and opposite of the output signal. This is represented graphically by additionally providing a vector component $V_{ABS}$ having a phase and magnitude that is substantially equal and opposite to the vector, $V_{out}$. This is effectively nullifying the output signal. However, the adjustable balance signal, $V_{ABS}$ can be varied to effectively reduce the output signal to below a predetermined compensated value. The type and nature of the adjustable balance signal will depend on the nature of the output signal. The simplest approach is where the output signal is sinusoidal in nature, e.g. derived from a tuned circuit and thus, the balancing signal is one selected to substantially cancel the sinusoidal wave. Where the drive signal is derived by a plurality of switches as found in a variable frequency metal detector, the output signal is in an uncontrolled shape and therefore, lacks any symmetry, i.e. more specifically the output signal adopts a more square or trapezoidal shape with one or more harmonics. Thus, establishing an adjustable balance signal to nullify or reduce the imbalance in the output signal is more complicated than where the output signal is sinusoidal in nature. Simply establishing an equal and opposite signal to cancel the output signal is not always appropriate in this case. The adjustable balance is varied to an extent that when combined with the imbalanced signal effectively reduces the signal to below a predetermined threshold value or nullify the output signal. The algorithms to achieve this can be more complicated than simply adding or subtracting the signals, as one would expect from a signal from a traditional tuning circuit. What is important in the present invention is that the resultant output from the combined adjustable balance signal and the imbalanced signal reaches below a predetermined threshold value.

Preferably, the adjustable balance signal is based on the drive signal having a phase and amplitude component that is adjusted so that it is substantially equal and opposite to the output signal. Preferably, at a given operational frequency of the metal detector, the adjustable balance signal is varied by increasing or decreasing the adjustable balance signal in sequential steps. At each step, the output signal is measured to see if it has reached below a predetermined threshold value. If not, the adjustable balance is incremented and the measuring process repeats to see if it has reached below a predetermined threshold value. Once the output signal reaches below a predetermined threshold value, the adjustments made to the adjustable balance signal at a given frequency are stored in a database or look-up table for later retrieval at that given frequency. By varying the adjustable balance signal through a trial and error process help to mitigate the complications in mathematically establishing a cancelling signal for any imbalance in the output signal.

Preferably, the process of calibrating the metal detector by nullifying the output signal or balancing the coil system is repeated for successive frequencies. Preferably, the frequency is varied incrementally, more preferably in substantially 10 Hz increments. This is made possible since the process of balancing the coil system is automated. More preferably, the adjustable balance signal can be varied by software. Whereas in prior art metal detectors only a select few frequencies are subjected to the balancing process due to the time and effort to physically adjust the separation of the coils to compensate for the level of imbalance, controlling and varying the adjustable balance signal through the use of software to quantitatively measure the level of imbalance of the coil system and automatically configure the drive signal to bring it into balance automates the balancing process and thereby a greater range of operational frequencies can be subjected to the balancing process.

Preferably, the adjustable balance signal is varied by a potentiometer, more preferably a digital potentiometer. The use of a digital potentiometer enables the adjustable balance signal to be controlled by software. This allows the system to automatically nullify any imbalance in the system, i.e. compensate the output of the coil system by the adjustable balance signal to provide a compensated signal. The use of one or more potentiometers allows the balancing signal to effectively compensate for any imbalance in the output signal irrespective of the shape or form of the output signal. This is even possible where the coil system is driven by a plurality of switches as taught in WO 2006/087510 (Spectrum Inspection Systems Limited), where the resulting square wave (or a trapezoidal wave) generates a large number of relatively high energy harmonics compared with the conventional sinusoidal signal generated by a tuned circuit. Preferably, the potentiometer comprises a first potentiometer and a second potentiometer and the adjustable balance comprises a first adjustable balance signal and a second adjustable balance signal. The first adjustable balance signal is varied by the first potentiometer and the second adjustable balance is varied by the second potentiometer. Preferably, the first adjustable balance signal is substantially not in phase with the second adjustable balance signal. More preferably, the first adjustable balance signal is out of phase with the second adjustable balance signal by equal to or less than substantially 90°. It has been found that the further apart the first and second adjustable balance signals from 90°, the more difficult it would be for the adjustable balance signals to balance any imbalance in the output signal. Preferably, the first adjustable balance signal is in phase with the drive signal and the second adjustable balance signal is not in phase with the drive signal. Preferably, the second adjustable balance signal is out of phase with the drive signal by substantially 90°. Equally, the first adjustable balance signal and/or the second adjustable balance can be set at any arbitrary angle that is not in phase with the drive signal or not in phase quadrature (90° out of phase with the drive signal) with the drive signal respectively. Varying the balance signal by two potentiometers allows the full 360° phase angle of the output signal to be covered. Optionally, the adjustable balance signal can be varied by a tuning circuit comprising a variable resistor (potentiometer), a variable capacitor and/or a variable inductor. In contrast to two potentiometers, a tuning circuit comprising a potentiometer, a variable capacitor and/or inductor only allows 90° phase angle variation of the drive signal to be covered.

More preferably, the adjustable balance signal is varied by an Electronic Programmable Logic Device (EPLD), e.g. a Complex Programmable logic device (CPLD) or Field Programmable Gate Array (FPGA). Coupled to an EPLD, a CPU selects a drive map stored in the EPLD or in the CPU which then sends signals to a driver to generate both drive signal and adjustable balance signal at a given working frequency. For example, the driver comprises a plurality of switches, e.g. FETs, such that through a selection of the drive map stored in the EPLD, the EPLD controls an internal clock oscillator to drive a plurality of switches, e.g. FETs, to create the transmitter drive signal at a given frequency. As the adjustable balance signal is derived from the drive signal, the adjustable balance signal will be at the same frequency as the drive signal. In addition for generating the drive signal and the adjustable balance at a given working frequency, the CPU coupled to the EPLD can also be used to vary the amplitude and phase of the generated adjustable balance signal. This removes the need for a potentiometer or tuning circuit as the variation in the adjustable balance signal can be done purely through use of programmable logic circuits (PLCs).

The adjustable balance signal in step (a) and/or the combined adjustable balance signal and/or the output signal in step (b) above is filtered by a low pass filter, more preferably a switchable low pass filter to cater for the different operating frequencies. Whereas in known autobalance systems, the system is based on a regular sinusoidal wave generated over a limited range of frequencies by means of a tuning circuit, the output from a variable frequency metal detector whereby the drive coil is driven by a plurality of switches, generates a square wave (or trapezoidal wave) with a large number of high energy harmonics or harmonic distortions along with the fundamental frequency of operation, i.e. the resultant wave typically has an uncontrolled shape. In absence of the low pass filter, the detector runs the risk that the peak signal voltage of the compensated signal as a result of the harmonics may exceed the predetermined threshold value of the compensated signal resulting in a continuous imbalance. More importantly, the peak signal voltage may exceed the saturation limit of the detection circuitry. The low pass filter filters out one or more harmonics from the adjustable balance signal and/or the output signal leaving the fundamental component, i.e. generates a more sinusoidal waveform that is more workable and measurable and is not disrupted by the high energy harmonics.

The adjustable balance signal and/or the output signal can each individually be filtered by one or more low pass filters to remove one or more harmonics from their respective signals prior to being combined to form the compensated signal. The low pass filter also allows the adjustable balance signal to be effectively varied by the potentiometer or PLC or otherwise so as to compensate for any imbalance in the output signal irrespective of their shape or waveform or the presence of any harmonic distortion. This simplifies the 'balancing' operation, because less steps are needed to reach a balanced state since the signal has a waveform that is more "manageable" (generates a more sinusoidal waveform) than a signal with a waveform having no regular shape.

During an initial start-up of the metal detector, the system scans through a range of operating frequencies and varies the adjustable balance signal by automatically adjusting the potentiometer at each given frequency necessary to balance the detection coil system. A database or look-up table is built up of stored adjustments of the potentiometer for different operating frequencies. A time delay can be provided before each measurement of the baseline signal in order to allow the frequency of the detection coil system to stabilise.

Preferably, the operating method for detecting metal contaminants comprises the step of:

a) selecting a desired frequency of operation in the absence of an object;

b) retrieving the stored adjustments made to the adjustable balance signal at the desired frequency from the database;

c) adjusting the adjustable balance signal to the adjustments in the database;

d) compensating the output signal for the adjustable balance single to provide the compensated signal.

The above process pertains to the product calibration stage whereby the metal detector, more specifically the coil system, is calibrated for a particular product type and involves selecting an operational working frequency for that product type so that the output signal from any metal contaminants embedded in the product can easily be distinguished from the output signal from the product alone. In absence of any products in the detector or for dry products, combining the adjustable balance signal with the output signal as a result of any imbalance in the coil system will result in the compensated signal, e.g. nullify the imbalance in the coil system. Once a desired frequency of operation is selected based on the characteristics of the product such as size, electrical conductivity, magnetic permeability, combining the adjustable balance signal with the output signal of the detector optionally comprises the step of subtracting the adjustable balance signal from the output signal. As discussed above, since the output signal is in an uncontrolled shape and therefore, lacks any symmetry, merely detecting whether the combined adjustable balance signal and the output signal reaches below a predetermined threshold value is normally required. In operation, the operator manually selects a desired frequency of operation through experience of the product type. Once the frequency of operation has been selected, the system searches the database to retrieve the stored adjustment of the potentiometer, PLC etc., at that corresponding operating frequency from the earlier signal balancing calibration stage described above. If the system realises that at the particular operating frequency, there is an imbalance in the detection coil system resulting in a residual or non-zero baseline signal, the system compensates the output signal by combining with the appropriate nullifying adjustable balance signal to provide a more accurate representation of the output signal. This prevents the imbalance in the detection coil system from affecting the measured output signal.

The product calibration stage further comprises the steps of passing a test product through the detector, measuring the output signal as a result of the interaction of the test product with the magnetic field between the detection coils and then storing the measured output signal. A test product is a product that is representative of the product under investigation with no known contaminant present. This is to provide a base signal for the product type such that any variance in the output signal, e.g. phase angle, from future similar products under investigation from this base signal is an indication of a metal contaminant. This is because a contaminant will interact differently with the magnetic field resulting in an output signal having a different phase angle from that of the product alone. Typically, similar products under investigation are placed on a conveyor belt and the output signal is measured and compared with the stored output signal (base signal) from the test product at that operational frequency to see if there is any variance from the base signal. For example, consider the signal derived from the drive signal to have a P component that is representative of the in-phase component of the drive signal and a Q-component that is representative of the phase quadrature component of the drive signal. In the particular embodiment described below, the P' and Q' components of the output signal are measured. The P' component represents the in-phase component of the output signal and the Q' component represents the quadrature component of the output signal. This should not be mistaken for a P component and Q component of the signal derived from the drive signal, discussed above. For example, the adjustable balance signal derived from the drive signal has a P component that is in phase with the drive signal and a Q component that is in phase quadrature with the drive signal. The phase angle of the output signal is determined from the measured P' and Q' values, e.g. by means of simple trigonometry. Further detail of the product calibration stage is described in the specific embodiment below.

The invention correspondingly provides a metal detector comprising a) coil system; b) a driver circuit for establishing an alternating magnetic field in the coil system so as to generate an output signal and an adjustable balance signal in the absence of an object at a given frequency and c) an adjustor for varying the adjustable balance signal at said given frequency so as to combine with the output of the detector to provide a compensated signal.

Preferably, the driver circuit is arranged to operate the coil system at any one of a selection of different frequencies. The sensitivity of a metal detector is determined by the ability of the metal detector to select an optimum frequency of operation for a particular product type. For example, whereas one product is detectable at one particular frequency, this is not the case at another frequency or for another product type. Moreover, whereas at one frequency a food product is successfully discriminated from a metal contaminant, this is not the case at another frequency. Thus for a given product type, the metal detector has to be able to switch through a range of frequencies in order to provide an optimum sensitivity of operation. The driver circuit comprises a plurality of switches being arranged to alternatively connect the coil system across a potential difference to cause the coil system to be driven at an operating frequency determined by the operation of the switches as described in the international patent application WO 2006/087510 (Spectrum Inspection Systems Ltd). Preferably, the plurality of switches can be field effect transistors (FETs) as taught in WO 2006/087510 (Spectrum Inspection Systems Ltd), bipolar junction transistors (BJTs) or any other suitable switching device. By controlling the input to the coil system using a plurality of switches, instead of the conventional tuned circuit, it is possible to program a processor or programmable controller to operate the plurality of switches so that any desired frequency of operation can be obtained in order to maximise the sensitivity of the metal detector. For example, as discussed in WO 2006/087510 (Spectrum Inspection Systems Ltd), the CPU monitors to see whether the detection coils are saturated or a metal contaminant is successfully discriminated in a test sample and in response to this, selects an appropriate frequency of operation. This would enable the metal detector to simply be installed and switched on, the metal detector monitoring its own operation and selecting an appropriate drive frequency for a particular product type. This would also permit different product types to be used with a detector, with the detector recognising when it is necessary to select a different frequency. Typically and as described above, during operation of a metal detector an operator will normally manually select a desired frequency of operation for a particular product type through experience. The driving of the coil system by means of a plurality of switches permits the operator to select an ideal frequency of operation from a greater range than traditionally using tuned circuits.

Preferably, the driver circuit comprises a microprocessor (CPU) and an electronically programmable logic device, the output of the electronically programmable logic device controls said switches, wherein for a particular detection coil, a plurality of drive maps is stored in the electronically programmable logic device each containing a switching sequence for the switches for a respective predetermined frequency of operation of the coil system, wherein the microprocessor selects an appropriate switching sequence depending on the selected frequency of operation. This provides a convenient way of ensuring the switches are controlled in a precise and predetermined manner for any frequency selected.

Preferably, the metal detector of the present invention comprises a microprocessor and an electronically programmable logic device for varying the adjustable balance signal at a given frequency and combining said adjustable balance signal with the output signal at said given frequency of the drive signal to provide a compensated signal. The electronically programmable logic device for varying the adjustable balance signal can be the same electronically programmable logic device as used for driving the coil system as discussed above. More sophisticated electronically programmable logic devices such as Complex Programmable logic device (CPLD) or Field Programmable Gate Array (FPGA) allow more complex operations to be performed. More preferably, the microprocessor is built into the metal detector. Alternatively, the microprocessor is provided by a personal computer. Preferably, the metal detector comprises a storage device for storing the adjustments made to the adjustable balance signal to provide the compensated signal. For example, take the example where the adjustable balance signal is varied by one or more potentiometers, then at each operating frequency the microprocessor stores the adjustments made to the potentiometer necessary to balance the detector coil system. A database or look-up table is thus built up showing the adjustments of the potentiometer and/or compensated signal for each corresponding operating frequency.

Preferably, the coil system comprises a drive coil and a detection coil so that in use when an alternating magnetic field is established in the coil system, the detection coil inductively couples with the magnetic field associated with the drive coil to generate an output signal. More preferably, the detection coil comprises at least a first and second detection coil at separate locations and arranged such that the presence of a metal will distort the magnetic field associated with the drive coil and produce an imbalance in the output of the detection coils resulting in a substantially non-zero output from the detection coils. The first and second detection coils are preferably arranged substantially in opposition and are electrically connected in series or parallel. By connecting the first and second detection coils in opposition, their induced voltages oppose one another and thereby cancel. If the coil system is in a perfectly balanced state their output signal is zero. In contrast, where the coil system is in an imbalanced state their output signal is substantially non-zero.

In addition to or in combination to calibrating the output signal to compensate for any imbalance in the output signal, in a second embodiment of the present invention the system preferably compensates for noise as a result of the delays in the interaction of the magnetic field with the product under investigation and the detection electronics and noise from moving metal. The present applicant has mitigated the above problems by providing a system that automatically compensates the output signal to take into account noise derived from delays through the interaction of the magnetic field with the product under investigation and the detection electronics and/or noise as a result of external influences disrupting the measurements in the detection coils, e.g. vibration. This noise is usually measured by recording the interaction of the magnetic field in the coil system with ferrite. In theory, the output signal from ferrite resembles the output signal as a result of noise. Thus by discriminating or compensating out the output signal from ferrite, signals responsible for noise can effectively be reduced or substantially reduced, i.e. the metal detector is compensated for any external disturbances to the coils. Thus, the compensated signal for noise will represent a fixed reference point from which future measurements are made. In the present invention, the term "compensated out" or "discriminated" is where the output signal is reduced to a substantially zero value or a near zero value.

In addition to the noise as a result of external influences acting on the coils, there is also delays in measuring the output signal in the detection electronics as a result of the interaction of the product under investigation with the magnetic field and subsequent recordal of its output signal. Without compensating for this delay, the phase angle of the output signal from a product under investigation would lag behind or lead the 'true' output signal if there were no delays in the detection electronics. Since the phase angle of the output signal is representative of the type of product or contaminant present between the coils, any delays in the phase angle results in wrongly identifying the type of product under investigation or contaminant. To cater for this delay, traditionally the phase angle of any product under investigation is measured with reference to a fixed reference signal at a given frequency. This reference signal is chosen so that a phase angle of zero degrees represents a product that is purely energy absorbing, e.g. a perfect or near perfect magnetic material. In theory, and everything being perfect, a perfect or near perfect magnetic material due to the interaction with the magnetic field should largely result in a reactive signal that is in phase quadrature with the resistive signal. However, due to this delay in the detection electronics, the output signal from a perfect magnetic material at a given frequency has a quadrature component but also a resistive component. Thus, if we consider the vector diagram shown in FIG. 1, the vector line corresponding to the output signal from a perfect magnetic material will lie between the resistive axis and the reactive axis. In view of this discrepancy, the output signal is adjusted so that the output signal from a perfect magnetic material is largely in the reactive region with minimal or no resistive component. The nearest best thing to a perfect magnetic material in the industry is ferrite material. Although not purely magnetic, the output signal from ferrite does provide a good reference point to tune the metal detector to favour an output signal in a given phase whilst eliminating those signals in phase quadrature to this direction. In fact, the output signal from ferrite generates an output signal that is largely reactive and therefore, the resistive component would largely be substantially zero or compensated out.

The present invention provides a method of operation of a metal detector wherein the output signal is automatically compensated for any delays or noise in measuring the output signal at given frequency, said output signal having a first component and a second component, the first component being out of phase with respect to the second component at a predetermined phase angle, wherein the output signal is compensated for any noise or delays in measuring the output signal at a given frequency by the steps of:

a. measuring the output signal in the presence of ferrite between the coil system,
b. digitally adjusting the output signal so that the output signal in the first or second component of the output signal is equal to or below a first predetermined threshold value and the output signal in the second or first component of the output signal is equal to or above a second predetermined threshold value,
c. storing the adjustments made to the output signal in a database or a look-up table,
d. repeating steps a, b and c for different frequencies.

Preferably, the output signal is digitally adjusted so that the magnitude of the output signal in the first or second component of the output signal is equal to or below a first predetermined threshold value and the magnitude in the second or first component of the output signal is equal to or above a second predetermined threshold value. By storing the adjustments made to the output signal as a look-up table or database removes the requirement to manually adjust the output signal to compensate for this delay. Preferably, the look-up table or the database is separate to the look-up or database used to calibrate for any imbalance in the output signal as discussed above. As this delay is usually characteristic of a particular metal detector, providing for this calibration can be carried out at the factory site prior to being shipped out to the customer's site, i.e. on first manufacture. By digitally compensating this delay factor in the measurement of the output signal but more importantly by storing the adjustments made to the output signal removes the need of repeatedly adding capacitors to a traditional tuning circuit in order to adjust the output signal so that in the presence of ferrite, the output signal will largely be the reactive component.

Preferably, the first component of the output signal is substantially in phase quadrature with the second component of the output signal. As the reactive component is in phase quadrature with respect to the resistive component, by adjusting the output signal having a first component that is in phase quadrature with a second component, it is possible to discriminate or compensate out the output signal from ferrite in either the first component or the second component of the output signal, leaving largely the output signal in the second or first component of the output signal. The term "compensated out" or "discriminated" represents the situation whereby the output signal is adjusted so that it is substantially zero or near zero (a minimum predetermined threshold value) at one phase angle with respect to the drive signal and the output signal is dominated at another phase angle with respect to the drive signal. This situation occurs when the phase angle between the first and second component of the output signal is substantially equal to 90°. When viewed on a vector diagram, the vector line representing the output signal is effectively rotated so that it lies substantially or nearby on the reactive axis having no or little resistive component. In this way, the output signal that is generated as a result of the interaction of ferrite with the magnetic field will largely be the reactive component. For example, setting the metal detector to detect a P' signal (first or second component) and a Q' signal (second or first component) whereby the P' component is in phase quadrature with the Q' component, then the metal detector is adjusted so that the output signal is largely the Q' signal or the P' signal, i.e. the reactive component, and little or no Q' or P' signal (resistive component). Thus, knowing that one of the components of the output signal from ferrite should read zero or near zero, the output signal is adjusted in the presence of ferrite at a given frequency so that it largely generates a reactive signal and a zero or near zero resistive signal (one of the components reads substantially zero and the output signal is dominated by its phase quadrature component). It is this relationship in measuring a maximum Q' or P' value and a minimum P' or Q' value in the presence of ferrite between the detection coils, that allows the system to compensate the system for any noise or delays in the detection system. However, this relationship in measuring the output signal is not restricted to adjusting the output signal so as to produce a substantially maximum first or second component when the second or first component of the output signal is substantially zero, i.e. at the condition where the first or second component is in phase quadrature with the second or first component of the output signal. The angle between the first and the second component of the output signal can be at any predetermined phase angle so as long as the system can identify a 'maximum and minimum' relationship between the two components of the output signal. Instead of adjusting the phase angle of the output signal from ferrite such that one of the components is substantially equal to zero (i.e. when the two components of the output signal are in phase quadrature), the output signal can be adjusted such that the first or second component of the output signal is equal to or below a first predetermined threshold value and the second or first component of the output signal is equal to or above a second predetermined threshold value. In this situation, the first component of the output signal is not in phase quadrature with the second component of the output signal but at another arbitrary phase angle. The first and second predetermined threshold value being largely determined by the phase angle between the first and second component of the output signal.

Preferably, the output signal is digitally adjusted so as to discriminate the output signal in the first or second component of the output signal such that the output signal in the first or second component of the output signal is substantially equal to zero. By compensating the resistive component out, any noise in the detection electronics will also be taken into account. In order to compensate the output signal in the first or second component of the output signal, preferably the metal detector comprises a phase sensitive detector, whereby the output signal is compensated for any delays or noise in measuring the output signal at a given frequency by the steps of;— a. generating a reference signal;
b. combining the reference signal with the output signal of ferrite in the phase sensitive detector at a given frequency
c. digitally adjusting the reference signal such that when combined with the output signal from ferrite, the output signal in the first or second component of the output signal is equal to or below a first predetermined threshold value and the output signal in the second or first component of the output signal is above a second predetermined threshold value;
d. storing the adjustments made to the reference signal in a database or look-up table;
e. repeating steps a, b, c and d at different frequencies.

By generating a reference signal based on the drive signal, the reference signal can be adjusted so that when combined with the output signal from ferrite in the phase sensitive detector, the output signal in the first or second component of the output signal is equal to or below a first predetermined threshold value and the output signal in the second or first component of the output signal is above a second predetermined threshold value.

Preferably, digitally adjusting the reference signal so as to discriminate the output signal in the first component or the second component of the output signal, i.e. substantially equal to zero. The first and second predetermined threshold value being largely determined by the cosine of the angle between the reference signal and the output signal. Thus, when the angle between the reference signal and the output signal is equal to 90°, the phase sensitive detector compares the reference signal and the output signal to produce a substantially zero value (Cosine 90°=0). Maximum value is obtained when the output signal is in phase with the reference signal (Cosine 0°=1). Preferably, the metal detector comprises a first and second phase sensitive detector and the reference signal comprises a first reference signal and a second reference signal such that at a given frequency the first reference signal is combined with the output signal in the first phase sensitive detector to produce a first component of the output signal and the second reference signal is combined with the output signal in the second phase sensitive detector to produce a second component of the output signal. By varying the first and/or second reference signal, an adjustment is reached whereby the 'maximum and minimum' conditions of the output signal in the presence of ferrite are met. More specifically, when the first reference signal is in phase quadrature with the second reference signal, then the output signal in the first or second component of the output signal is compensated out or discriminated to largely read a zero or near zero signal and the output signal from ferrite will be dominated by either the output signal in the second or first component of the output signal that has not been compensated out, i.e. the reactive component. In other words, the output signal is effectively rotated so that it lies substantially or substantially superimposes on the reactive axis. Preferably, the reference signal, more specifically, the first and/or second reference signal, are increased incrementally and the output from the first and second phase sensitive detectors are monitored to establish whether the output signal in the first or second component of the output signal is equal to or below a first predetermined threshold value or has been compensated out, i.e. reads substantially zero. When the output signal in the first or second component has reached below a predetermined threshold value or has been compensated out, the output signal in the second or first component is above a second predetermined threshold value or has reached a maximum value. Preferably, the first reference signal is substantially in phase quadrature with the second reference signal to mimic the fact that the reactive signal is substantially in phase quadrature to the resistive signal, such that when combined with the output signal in the first and second phase sensitive detectors respectively, the first component of the output signal is substantially in phase quadrature with the second component of the output signal. By compensating out the output signal from ferrite in the first or second component, results in a signal that is purely reactive and therefore takes into account the delays in the detection electronics. Each time the output signal is compensated out/discriminated or reached below a first predetermined threshold value in the first or second component of the output signal (depending which component of the output signal is substantially in phase quadrature with the reference signal) at a given frequency, the adjustments made to the reference signals at that given frequency is stored in a database or look-up table for later retrieval. This represents the fixed reference point from which future products under investigation are measured. As the nature of the noise or the delays in the detection system varies with frequency, this is repeated at different operational frequencies of the metal detector.

Preferably, the reference signal is digitally adjusted by incorporating a delay factor in the reference signal. Where the reference signal in based on the drive signal generated by an Electronically Programmable Logic Device (EPLD), then the adjustments can be made by incrementally adjusting the high speed counter or drift register of the EPLD.

In operation when scanning a product to detect metal on, in or associated with that product, the method preferably comprises the steps of:

a. retrieving the adjustments made to the output signal at a desired operational frequency of the metal detector from the database or look-up table;

b. adjusting the output signal to the adjustments stored in the database or look-up table so to compensate for any noise or delay in measuring the output signal.

During scanning a product under investigation to detect for metal contamination at a given operational frequency of the metal detector, the system (e.g. processor) retrieves the adjustments made to the output signal from the database or look-up table and subsequently adjusts the output signal to the adjustments stored in the database or look-up table so as to compensate for any delay in measuring the output signal. Preferably, the phase and/or magnitude of the output signal are compensated for the adjustments stored in the database or look-up table. Following compensation of the output signal, the measured output signal in a first or second component of the output signal as a result of the interaction of the product under investigation with the magnetic field will represent the "true" first or second component of the output signal that has been compensated for any noise or delays. Likewise, the measurement of the second or first component of the output signal as a result of the interaction of the product with the magnetic field represents the "true" second or first component of the output signal that has been compensated for any noise or delays. Without any form of compensation, the first or second component of the output signal and the second or first component of the output signal will either lead or lag behind the "true" first and/or second components of the output signal.

Each time the metal detector is used to test products under investigation at a given frequency, the metal detector, more particularly the processor, retrieves the appropriate correction factor from the look-up table and makes the appropriate corrections to the output signal, more specifically to the reference signal, to compensate for any noises or delays in the output signal. Preferably, the phase and/or magnitude of the output signal are compensated for the adjustments stored in the database or look-up table. More specifically, the output signal is calibrated to a fixed reference point so that any measurements made from products under investigation at a given frequency are made relative to this fixed reference point. Preferably, the adjustments to the output signal to compensate for any noise or delays in the output signal discussed in the second embodiment of the present invention can be used in conjunction with compensating for any imbalance in the output signal as discussed with the first embodiment of the present invention.

As discussed with the first embodiment of the present invention, the metal detector can be a variable frequency metal detector whereby the driver circuit comprises a plurality of switches arranged to cause the coil system to be driven at a frequency determined by the operation of the plurality of switches. As a variable frequency metal detector operates over a large frequency range, digitally compensating for any noise or delays in the output signal offer significant benefits over traditional metal detectors based on tuning circuits both in terms of efficiency and accuracy of measurement.

Preferably, the metal detector comprises a rectifier to convert the output signal of the detection coil to a direct current (DC), so that the signal can be digitized. This enables the output signal to be read by the microprocessor (CPU).

SPECIFIC DESCRIPTION

Further preferred features and aspects of the present invention will be apparent from the claims and the following illustrative description made with reference to the accompanying drawings.

BRIEF DESCRIPTION OF THE DRAWINGS

FIG. 8b is a vector diagram depicting the vector lines representing the adjustable balance signals, Vbal1 and Vbal2, adjusted by the potentiometers, Pot1 and Pot 2 in FIG. 8a.

DETAILED DESCRIPTION

Figure 6:
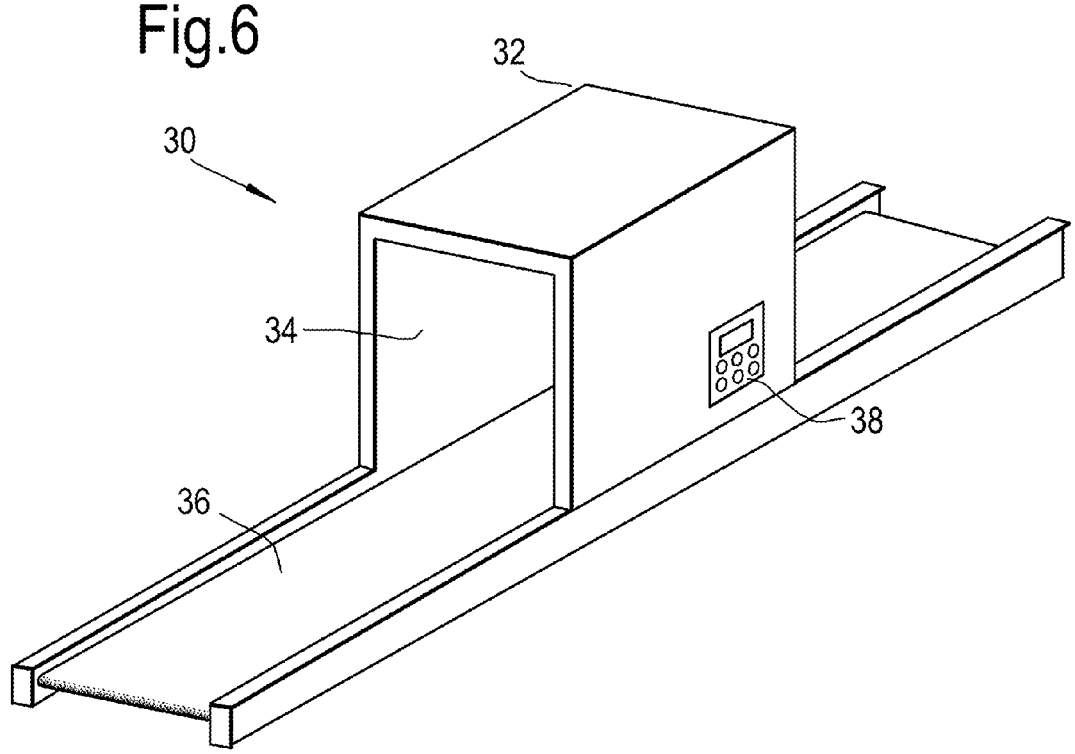
FIG. 6 is a perspective view of a metal detector apparatus and belt conveyor embodying the present invention.

A typical metal detection apparatus 30 is shown in FIG. 6 and comprises a search head 32 with an aperture 34 through which the product on a conveyor belt 36 passes and a control unit 38 which processes the signals from the head. Inside the search head is a coil system (not shown) consisting of three coils surrounding the aperture and wound on a non-metallic frame. The coil system comprises a central drive or transmitter coil and detection coils either side of the drive coil. The receiver/detection coils are generally identical and placed the same distance from the transmitter coil such that the changing magnetic field provided by the drive or transmitter coil induces a voltage in the receiver coils. As taught in WO 2006/087510 (Spectrum Inspection Systems Ltd), the detection coils are arranged in a plane perpendicular to the direction in which the product is to pass and electrically connected in parallel and each detection coil is located on one side of the product only. When the detection coils are connected in opposition, their output is cancelled, resulting in a zero value, i.e. the detector coil system is said to be in a perfectly balanced state. Depending upon the arrangement of the coil system, the detection coils are connected in opposition so that their induced voltages cancel. By connecting the detection coils in parallel as described and shown in WO 2006/087510 (Spectrum Inspection Systems Ltd), in contrast to the more conventional series arrangement, the apparent power of the output signal is the same as for the series arrangement but the impedance value for the two coils is one quarter of that for an equivalent series arrangement. This greatly reduces the harmonics picked up by detection coil, which is particularly important when the drive coil is driven by a plurality of switches.

In the particular embodiment, the drive coil is arranged in a plane perpendicular to the product conveying direction and which is driven by a powerful oscillator capable of generating a strong high frequency field within the aperture through which the product passes.

In the particular embodiment the frequency at which the drive coil is driven is determined by a plurality of switches. A microprocessor or controller is arranged to alternatively connect the drive coil directly across a potential difference to cause the drive coil to be driven at an operating frequency determined by the operation of the switches as described in the international patent application WO 2006/087510 (Spectrum Inspection Systems Ltd). The switching of the plurality of the switches is such that during each half cycle of the drive signal, the potential difference applied across the drive coil is reversed. By controlling the input to the coil system using a plurality of switches, it is possible to program the controller to operate the plurality of switches so that any desired frequency of operation can be obtained. Moreover, driving the coil by means of a plurality of switches allows the drive coil to be driven at a greater number of frequencies than can be achieved from a single traditional tuning circuit.

Figure 7:
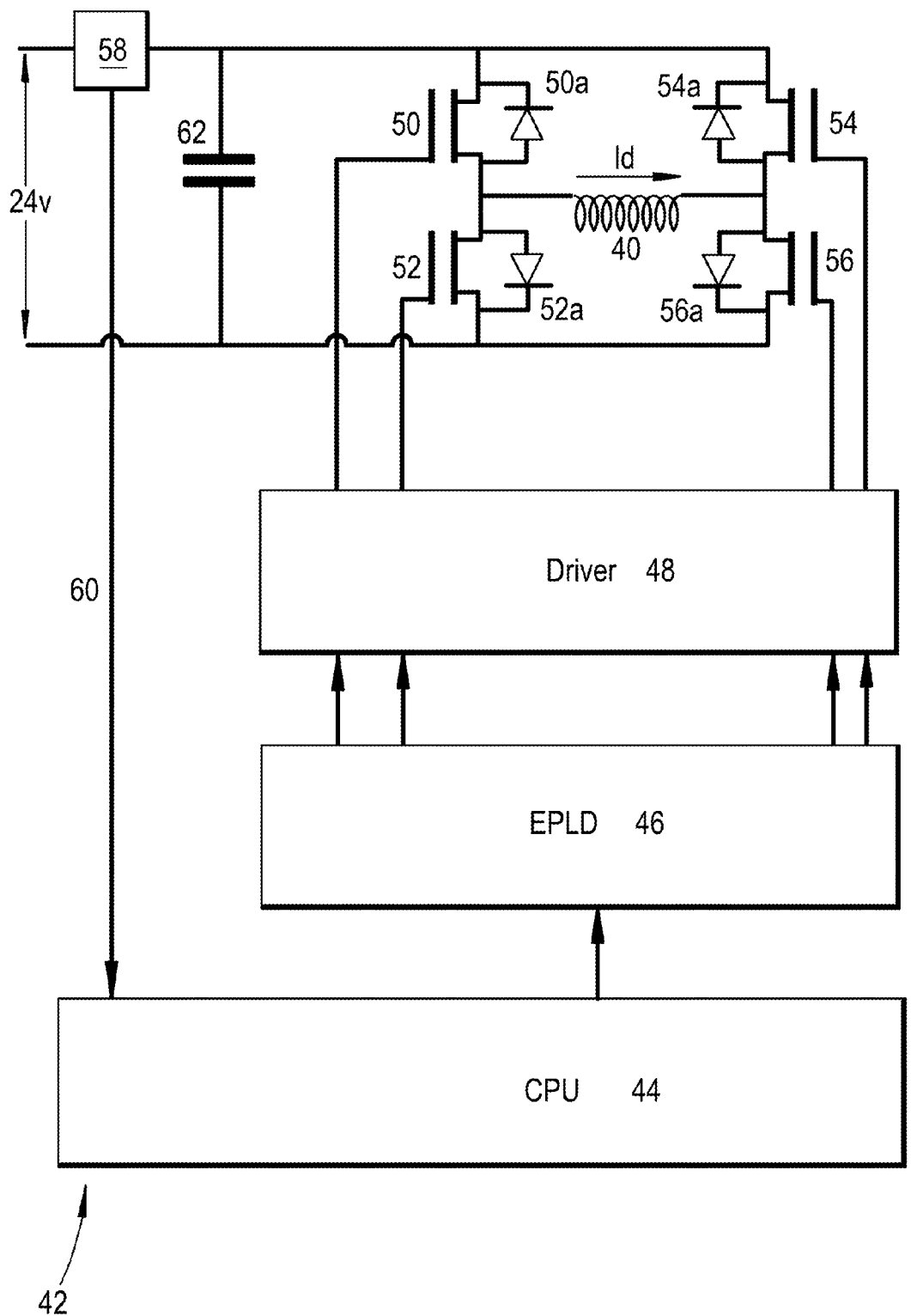
FIG. 7 is a circuit diagram showing the driver circuit of the apparatus of an embodiment of the present invention.

Referring to FIG. 7, the drive coil 40 is controlled by a driver circuit 42 and the driver circuit 42 comprises a central processing unit (CPU) 44, an electronically programmable logic device (EPLD) 46 and a driver 48 connected to four field effect transistors (FETs) 50, 52, 54, and 56 forming a plurality of switches. The four FETs 50 to 56 form a full wave bridge circuit across a conveniently chosen potential difference, with the drive coil 40 connected across the output of the bridge circuit. For example, the potential difference can be conveniently chosen to be 24 volts. The potential difference establishes a drive current Id across the drive coil 40.

Alternative switching arrangements can be used instead of the use of four FETs to form a full wave bridge shown in FIG. 7. For example, the FETs can be arranged to form a half wave bridge (not shown) whereby two FETs are only used to form one end of the bridge and the other end is set to 0 volts. With the drive coil 40 connected across both ends, the switching is arranged such that the current Id flows through one FET via the drive coil in one half cycle and through the other FET in the other half cycle. Instead of FETs other types of switching devices are permissible in the present invention, e.g. the use of bipolar junction transistors (BJT). Additionally, a current sensor 58 is connected in the power supply, the output of which provides a signal on the line 60 back to the CPU 44. The circuit 42 additionally comprises four diodes 50a to 56a connected across respective FETs 50 to 56 and capacitor 62 connected across the supply. The CPU 44 in dependence upon information stored in look-up tables selects one drive map stored in the electronically programmable logic device 46 which then sends appropriate signals to the driver 48 to repeatedly control operation of the FETs 50 to 56 in a predetermined manner. In operation, the CPU 44, EPLD 46 and drive circuit 48 produces square waves of precise frequencies and phase relationships as required by the application. Further operation of the driver circuit 42 of FIG. 7 is described in WO 2006/087510 (Spectrum Inspection Systems Ltd).

Figure 3:
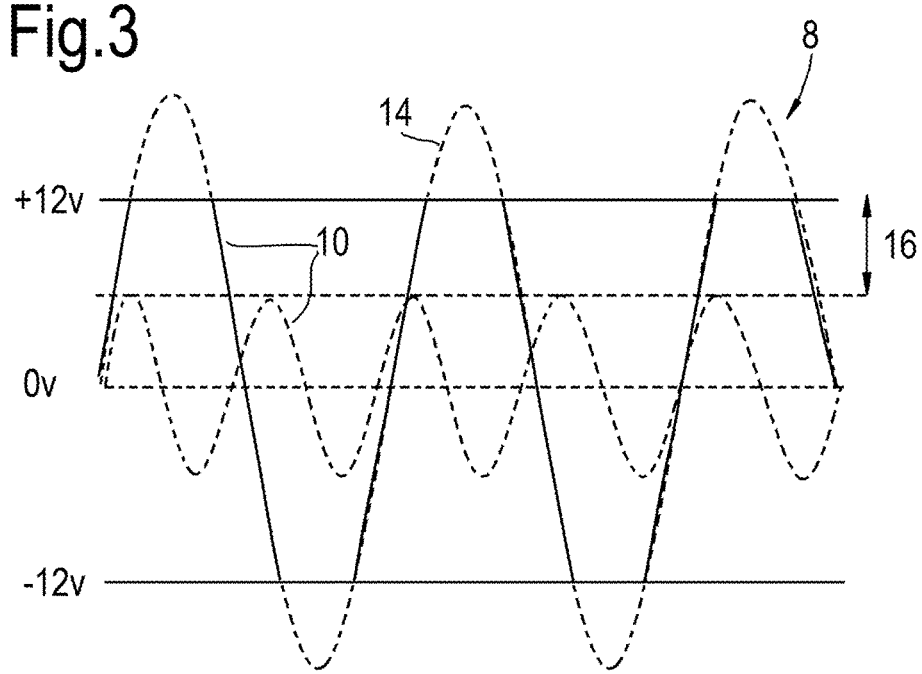
FIG. 3 is a schematic representation of the waveform of the output signal in the detection circuitry.
Figure 4:
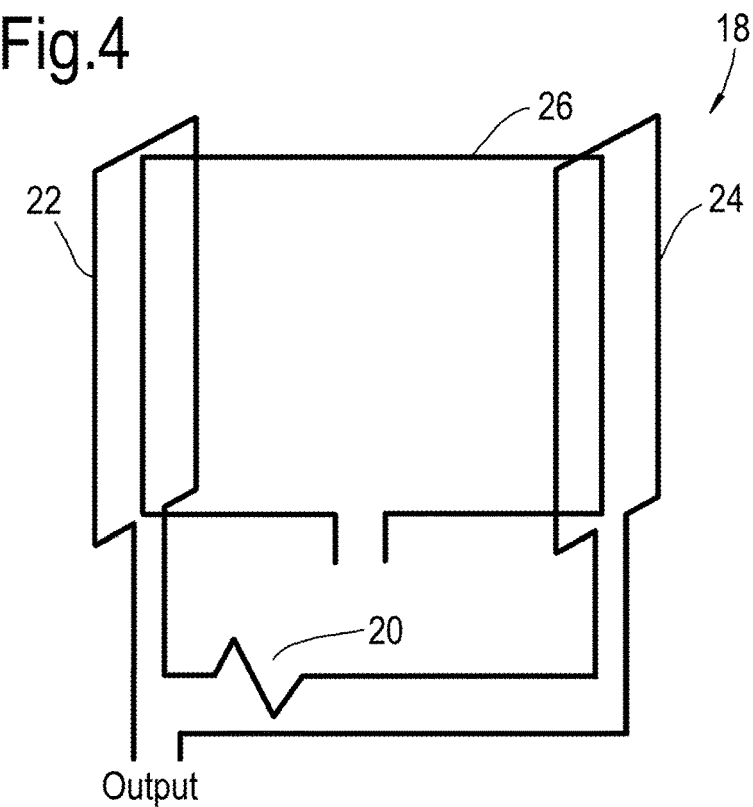
FIG. 4 is a perspective view of the coil arrangement in the search head of a metal detector showing a mechanical balance located between the detection coils.
Figure 5:
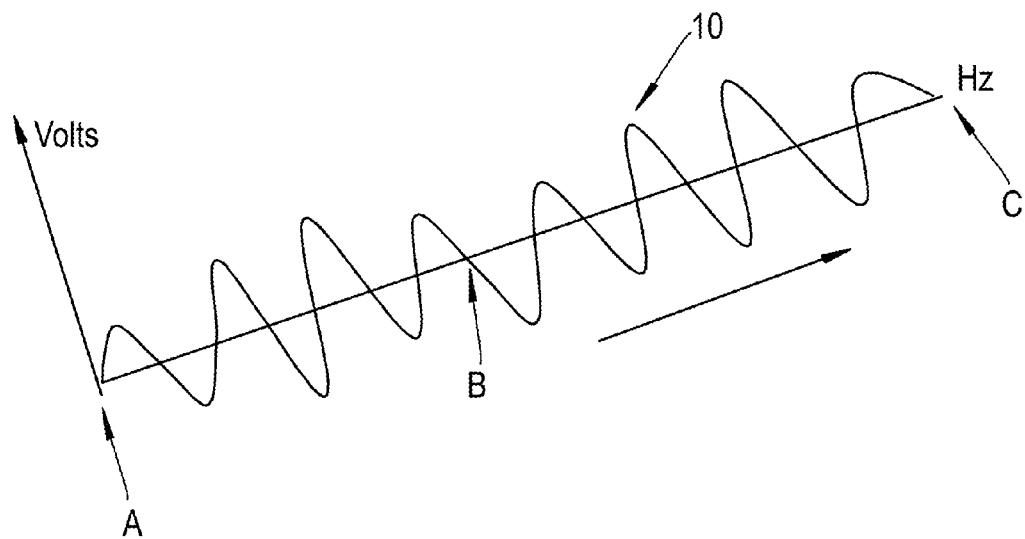
FIG. 5 is a schematic representation of the waveform of the output signal in the detection circuitry for a range of operational frequencies.

Detection circuitry such as detection coil amplifiers, phase sensitive detectors etc., of the detection coils processes the output signal from the detection coils to be fed into a level detector which provides a feedback loop to the CPU for the determination of the presence of metal contamination and its type. To mitigate detection inaccuracies as a result of the detection coils being out of balance, the present invention provides an automatic balance system which can be controlled largely by software and thereby allow the automatic balance system to balance the coil system at a greater number of frequencies, i.e. smaller increments between each successive frequency, than is practicable from a purely mechanical type balance. The present applicant has realised that by generating an adjustable balance signal based on the drive signal whereby the phase and/or amplitude of the adjustable balance signal can be adjusted/varied so that when combined with the output signal of the coil system at a given frequency, an amplitude and phase can be found such that when the balance signal is combined with the output signal of the coil system at the given frequency will produce a resultant balanced signal below a predetermined value. This is repeated for a number of operational frequencies of the detector and for each frequency, the adjustments made to adjustable balance signal necessary to produce the resultant balanced signal is stored for recall when that particular frequency is used in operation. As the output signal has a phase component and a magnitude component, balancing the system may involve compensating any one of the phase or magnitude component or both to bring the output signal to a balanced state in the absence of an object, e.g. using vector or coordinate algebra. The balanced state of the detection coils is not necessarily restricted to zero and any chosen value of the output signal capable of providing useful measurement results is applicable in the present invention. Moreover, by significantly reducing the output signal, the present invention also helps to prevent the output signal from saturating the detection coil amplifiers. More importantly, reducing or nullifying the output signal in absence of any products between the detection coils effectively increases the "headroom" voltage signal for detection of contaminants without saturating the detection coil amplifiers, i.e. provides more flexibility in 'turning-up' the drive signal (operating over a larger voltage range and thereby, increases the sensitivity of the metal detector for the detection of metallic contaminants). For example, a metal detector having a detection circuitry with a peak-to-peak signal detection range beyond which the detection circuitry will saturate, the present applicant has found that a threshold output signal or compensated signal of less than substantially 40% peak-to-peak of the signal range of the detection circuitry in absence of any products between the detection coils, more preferably substantially less than 10%, allows enough "headroom" voltage in the detection circuitry for the detection of contaminants without saturating the detection amplifiers. For example, a typical metal detector whereby the detection circuitry operates in the range +12 volts to −12 volts as shown in FIG. 3, the compensated signal is substantially less than 40% of 12 volts (4.8 volts), preferably substantially less than 15% of 12 volts (1.8 volts), more preferably substantially less than 10% of 12 volts (1.2 volts). This will allow substantially 7.2 headroom voltage or substantially 10.2 headroom voltage or substantially 10.8 headroom voltage respectively for detection purposes.

There are numerous ways to vary the adjustable balance signal so that when combined with the output signal it effectively nullifies the output signal. The term "combined" covers superimposing or multiplying or addition or subtraction or any combination thereof. When the drive coil is driven by a plurality of switches (i.e. a variable frequency metal detector), the output signal is in an uncontrolled format generally having a square shape (or trapezoidal shaped wave) in addition to one or more harmonics. Thus, to mathematically establish an equal and opposite signal to counter act any imbalance in such a signal would be difficult. The present applicant has realised that by generating one or more adjustable balance signals that can be varied in successive steps through a 'trial and error' process, an adjustable balance signal can be established that will effectively nullify any imbalance in the output signal or reduce it to below a predetermined threshold value. The following describes three examples of how the adjustable balance signal may be varied to combine with and effectively nullify the output signal.

FIG. 8 shows a circuit diagram 70 of a first embodiment of the present invention, which is an adaption of the circuit diagram described in the international patent application WO 2006/087510, and thus the components in common behave similarly. In summary, the driver circuit shown in FIG. 7 is represented by the dashed outline/box 42. The driver circuit 42 comprises a central processing unit (CPU) 44, an electrically programmable logic device (ELPD) 46 and a driver 48 connected to four field effect transistors (not shown) for simplicity. For simplicity, the driver 48, FETs (50 to 56) and the diodes (50a to 56a) of FIG. 7 are represented as the "driver" 48. The EPLD 46 stores a plurality of drive maps, each drive map containing a switching sequence for the switches (FETs) to drive the drive coil 40 at a respective predetermined operation of frequency of the metal detector. The CPU 44 selects an appropriate drive map from a plurality of drive maps stored in the electronically programmable logic device 46 to control the operation of the switches in a predetermined manner depending upon the frequency of operation of the driver circuit 42. Alternatively, the drive maps can be stored in the CPU. Once an appropriate drive map is selected, the drive map controls an internal clock oscillator of the EPLD so as to control the operation of the FETs in a predetermined manner depending upon the frequency of oscillation of the clock oscillator. The FETs enable the driver circuit 42 to provide a range of frequencies at which the coil system is to be operated. This provides a convenient way of ensuring the switches are controlled in an appropriate and precisely predetermined manner for any frequency selected. The EPLD 46 can be any suitable programmable logic device. In the particular embodiment, the EPLD can be a Complex Programmable Logic Device (CPLD) or a more sophisticated Field Programmable Gate Array (FPGA).

Figure 8A:
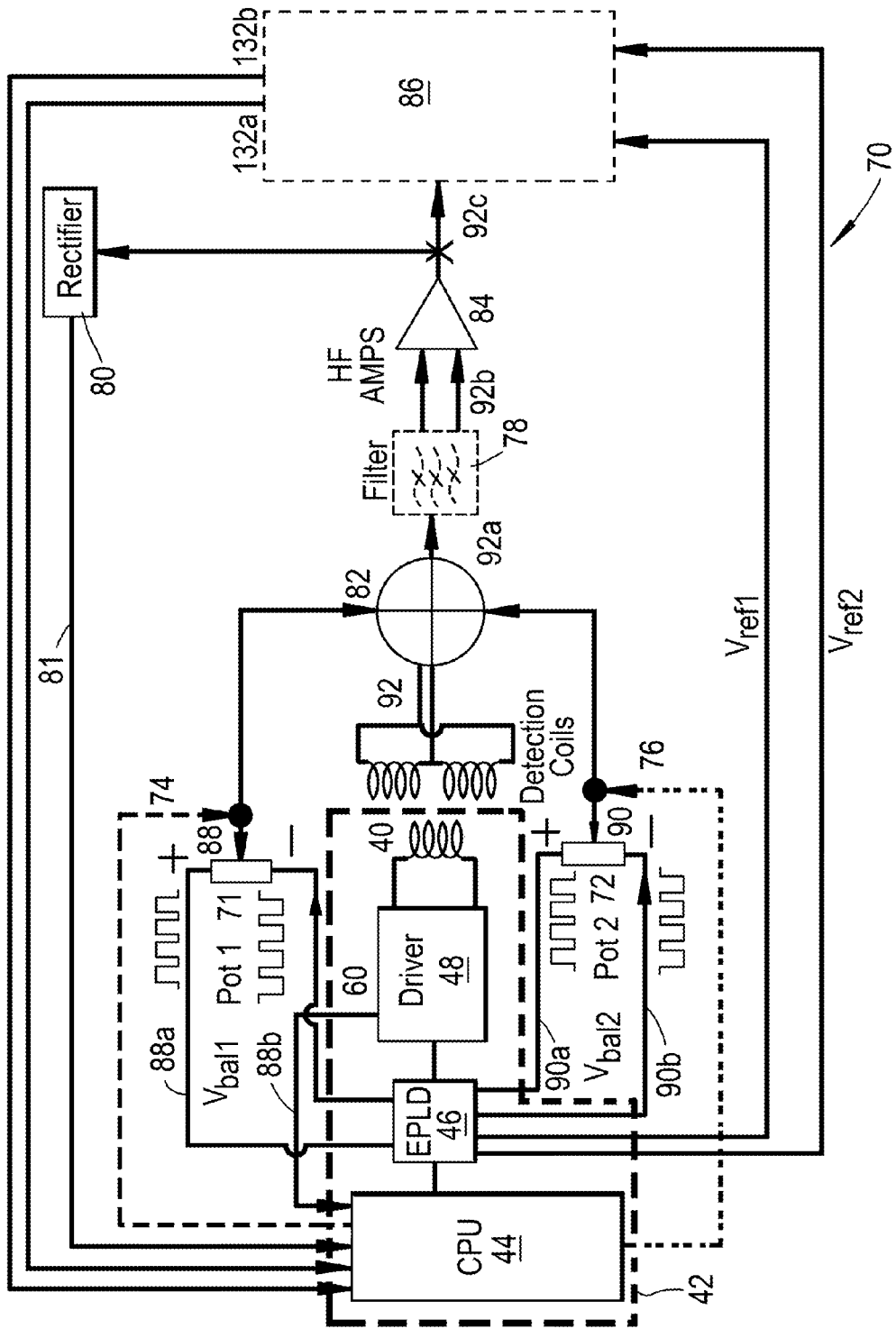
FIG. 8a. is a circuit diagram showing means to generate and adjust the adjustable balance signal to combine with the output signal of the coil system according to a first embodiment of the present invention.

The driver circuit 42 then creates a drive signal of varying frequency as discussed above to drive the drive coil. In addition to the signal to drive the drive coil 40, the CPU 44 in conjunction with the EPLD 46 is used to establish an adjustable balance signal based on the drive signal. As the adjustable balance signal is derived from the drive signal, it will operate at the same frequency as the drive signal. This is represented in FIG. 8a as line 88 and 90. Thus, the drive signal and the adjustable balance signal have the same frequency but with a fixed phase relationship with respect to each other. In the particular embodiment, the driver circuit 42 generates two balance signals, a first adjustable balance signal, Vbal1 (88) and a second adjustable balance signal, Vbal2 (90). $V_{bal1}$ 88 represents the in-phase component (P-signal) of the drive signal and conversely, $V_{bal2}$, 90 represent the quadrature component (90° out of phase, Q-signal) of the drive signal. The two balance signals, $V_{bal1}$ and $V_{bal2}$, can be then be adjusted or varied to an extent that when combined or superimposed with the output signal 92 of the detection coils effectively balances the coils, i.e. nullifies any imbalance in the coils. $V_{bal1}$ and $V_{bal2}$ are known as an adjustable balance signal or corrective signal. In the particular embodiment shown in FIG. 8a, the adjustable balance signal is varied or adjusted by two potentiometers, Pot 1 (71) and Pot 2 (72). Preferably the potentiometers are digital potentiometers 71, 72 so as to enable the potentiometer to be controlled by software or like means. In the particular embodiment, Pot 1 (71) and Pot 2 (72) are controlled by the CPU via the dashed lines 74 and 76 respectively. The ends of Pot 1 (71) are connected so as to vary the amplitude of Vbal1 throughout the range −P to +P whereby +P and −P are 180° out of phase with each other. The adjustable balance signal 88 and 90 are broken into two parts depending upon their phase relationship with the drive signal. For example, one end of Pot 1 is fed by a component of the adjustable balance signal that is in phase 88a with the drive signal and the other end fed (or represented) by the substantially −180° out of phase 88b of the drive signal, so by controlling the position of the wiper (sliding contact) of the potentiometer, $V_{bal1}$ can be varied throughout the range 0° to −180°. The different waveforms of +P and −P can be graphically represented as square waves in FIG. 8a. Conversely, the amplitude of the quadrature component ($V_{bal2}$) of the drive signal can be varied by Pot 2 (72) so that it covers the range +Q to −Q and therefore, +Q and −Q are 180° out of phase (see FIG. 8a). As with Pot 1, the ends of Pot 2 (72) are fed by the adjustable balance signal Vbal2 having components respectively representing the +90° (90a) and −90° (90b) of the quadrature component of the drive signal, so that $V_{bal2}$ can be varied throughout the range +90° to −90°. Thus, by varying $V_{bal1}$ and $V_{bal2}$ the full 360° phase angle range in both the in-phase component and the quadrature component of the drive signal can be covered.

Figure 8B:
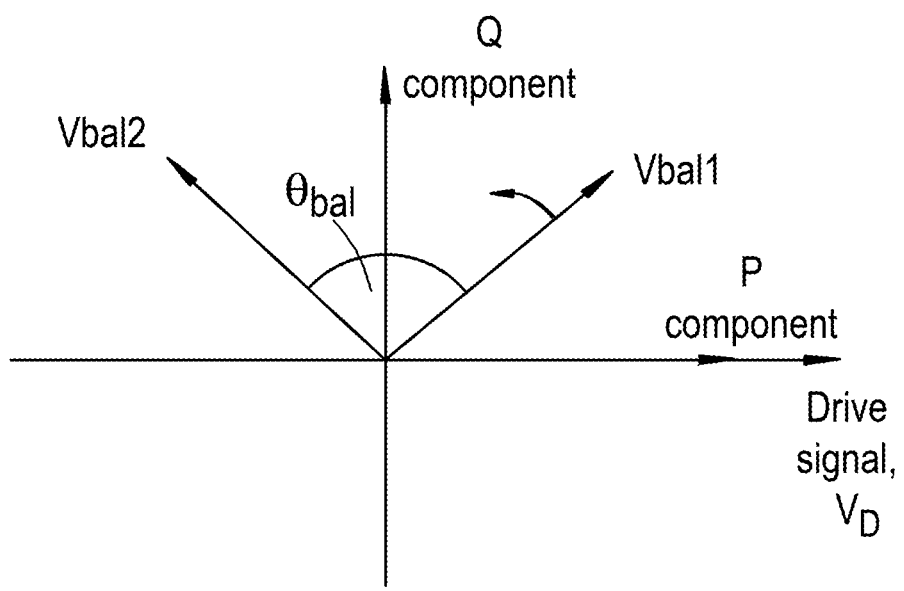

The present applicant has found that by varying the amplitude of $V_{bal1}$ and/or $V_{bal2}$, a setting is eventually reached such that when combined or superimposed with the output signal of the detection coil, effectively or substantially nullifies the output signal. In an ideal situation, the output signal should read zero if the system is in a perfectly balanced state. However, where the reading of the output signal is non-zero, the system compensates for any deviation in the output signal by combining it with the adjustable balance signal. It is not necessary that the ends of Pot 1 (71) and Pot 2 (72) are fed by the adjustable balance signal having a phase angle relationship with the drive signal as described above. What is essential is that the adjustable balance signal Vbal1 and/or Vbal2 can be varied by Pot 1 and Pot 2 to an extent that when combined or superimposed with the output signal of the detection coil effectively or substantially nullifies the output signal or reduces the output signal to a balanced condition (predetermined threshold value). For example, the signal fed to one end of Pot 1 (71) does not need to be in phase with the drive signal and thus, the signal fed to (or represented by) the other end of Pot 1 (71) does not need to be 180° out of phase with the drive signal. Any phase angle can be chosen relative to the drive signal so that Pot 1 covers the range 180°. Likewise, the quadrature component (Vbal2) of Pot 2 (72) does not need to be in phase quadrature with the drive signal as long as Pot 2 covers the range 180°, i.e. −90° to +90°. $V_{bal1}$ can be adjusted so that one end of Pot 1 (71) can be at any arbitrary phase angle with respect to the drive signal. Likewise, $V_{bal2}$ can be adjusted so that one end of Pot 2 (72) can be at another arbitrary phase angle with respect to the drive signal. As an example, $V_{bal1}$ can be adjusted so that one end of the Pot 1 (71) can be set at +45° with respect to the drive signal and therefore, if Pot 1 covers the 180° range, the other end of Pot 1 would be at +225° with respect to the drive signal. Likewise $V_{bal2}$ can be adjusted so that one end of Pot 2(72) can be set at 110° with respect to the drive signal and therefore, if Pot2 covers the 180° range, the other end of Pot2 would be at +290° with respect to the drive signal. In all cases the first adjustable balance signal, Vbal1, is not in phase with the second adjustable balance signal, Vbal2. If shown schematically on a vector phase diagram (see FIG. 8*b*), the vector lines representing the first adjustable balance signal, Vbal1 and the second adjustable balance signal, Vbal2 are separated by a predetermined fixed phase angle, $\theta_{bal}$, but the vectors lines can be rotated about the origin, each rotation of the vector lines representing a different arbitrary angle of Vbal1 and Vbal2 with respect to the drive signal. The P component and Q component shown in FIG. 8*b* represents the signal in-phase (0°) with the drive signal and the signal in-phase quadrature (90°) with the drive signal respectively.

In the particular embodiment, combining both signals (the adjustable balance signal 88, 90 and the output signal 92) involves superimposing the adjustable balance signal 88, 90 with the output signal 92 in a voltage adder 82 as is commonly known in the art to produce a combined output signal 92*a*. Combining the signals involves calculating the difference between the adjustable balance signal 88, 90 and the output signal 92 of the detection coils. Schematically this can represented by the vector diagram in FIG. 1. An imbalance in the detection coils is represented by the vector, Vout, having an amplitude determined by the length of the vector and a phase angle. To nullify the output signal, Vout, in absence of any products between the detections coils or for "dry products", the adjustable balance signal, $V_{ABS}$, is varied such that its amplitude and phase angle are substantially equal and opposite to the output signal, Vout.

Following amplification in the HF (high frequency) amplifier 84, the combined output signal 92*c* is measured by the CPU 44 via the line 81 to determine whether the coil system is in a balanced state. However, detection of metal requires a strong magnetic field alternating at the required frequency. Such a field is set up by the current through the drive coil, and is proportional to the voltage across it. The field contains a considerable harmonic content along with the fundamental frequency of operation. This is exacerbated where the drive coil is driven by a plurality of switches. More importantly, there is the risk that the peak signal voltage of the combined output signal 92*a* as a result of the harmonics may saturate the detection circuitry of the metal detector. To prevent one or more of the harmonics triggering an out of balanced signal and thereby causing confusion to the determination of whether the coil system is in a balance state or not, a low pass filter 78 is used to filter out the harmonics prior to amplification by the amplifier 84 so leaving the fundamental component 92*b*, i.e. generates more of a sinusoidal waveform that is more "workable" and measurable than a signal with a waveform having an irregular shape. Although not shown in FIG. 8*a*, alternatively to or in addition to having a low pass filter 78 to filter out the harmonics from the output signal 92*a* following the voltage adder 82, the output signal 92 and/or the adjustable balance signals 88, 90 can each be individually filtered by low pass filters prior to being combined by the voltage adder 82. In contrast to the previous arrangement as shown in FIG. 8*a*, by individually filtering the adjustable balance signals, 88 and 90, and/or the output signal 92 to remove the harmonics, allows the adjustable balance signal to be effectively varied by the potentiometers or PLC or otherwise so as to compensate for any imbalance in the output signal irrespective of their shape or waveform. Since the fundamental signal is more "workable" following removal of the harmonics, this has the advantage in reducing the number of adjustments needed to bring the output signal into balance. In the particular embodiment, the low pass filter is a switchable low pass filter 78 so as to be switchable at different operating frequencies. In the case where the drive coil is driven by a tuned circuit generating a sinusoidal output signal, little or no harmonic distortions are generated, and thus, the requirement of a switchable low pass filter may not strictly be necessary.

To enable the CPU 44 to measure the output signal, the output signal 92*c* is then rectified by a rectifier 80 (see FIG. 8*a*) to convert the alternating signal to a DC signal. The measuring point is taken from point X in FIG. 8*a*. The rectified signal is read by the CPU 44 via an analogue to digital converter (not shown). The magnitude of the DC signal enables the CPU to determine the degree of imbalance of the detection coil system. Removal of the harmonics from the output signal greatly improves the measurement of the output signal by removing any unwanted background noise from the signal. A feedback loop via the line 81 to the CPU, enables the CPU to adjust the setting of one or both of the potentiometer 71, 72 via lines 74 and 76 in response the measurement of the output signal. By means of a digital potentiometer, the adjustable balance signal can be controlled by software. If the CPU notices a non-zero value or that it is in an imbalanced state, the CPU varies the adjustable balance signal by continually adjusting the digital potentiometers, 71, 72, until the output signal reaches a zero or below a threshold value. One example of varying the adjustable balance signal is to incrementally vary Potentiometers 71 and 72 at successive steps, and each time the digital potentiometers are varied, the output signal is measured until a compensated signal is reached. Once the output signal has been nullified or reached below or equal to a pre-determined value at a given frequency, the CPU stores the adjustments made to the potentiometers, Pot 1 (71) and Pot 2 (72) at that frequency. More particularly, once the output signal is nullified or has reached a minimum threshold value at a given frequency, the adjustments made to the potentiometers (71, 72) are stored in a database or look-up table.

Also shown in FIG. 8*a*, the EPLD coupled to the CPU establishes two reference signals $V_{ref1}$ and $V_{ref2}$ which are input into detection circuitry 86 shown as a dashed box for establishing the presence of metal contaminants. In addition to creating the transmitter drive signal for driving the FETs and the adjustable balance signal discussed above, the EPLD also creates the reference signals, Vref1 and Vref2 which are input into the detection circuitry 86. As these signals are derived from the drive signal, they all have the same frequency but with a fixed phase relationship. Further detail of the detection circuitry 86 is discussed later.

Figure 9:
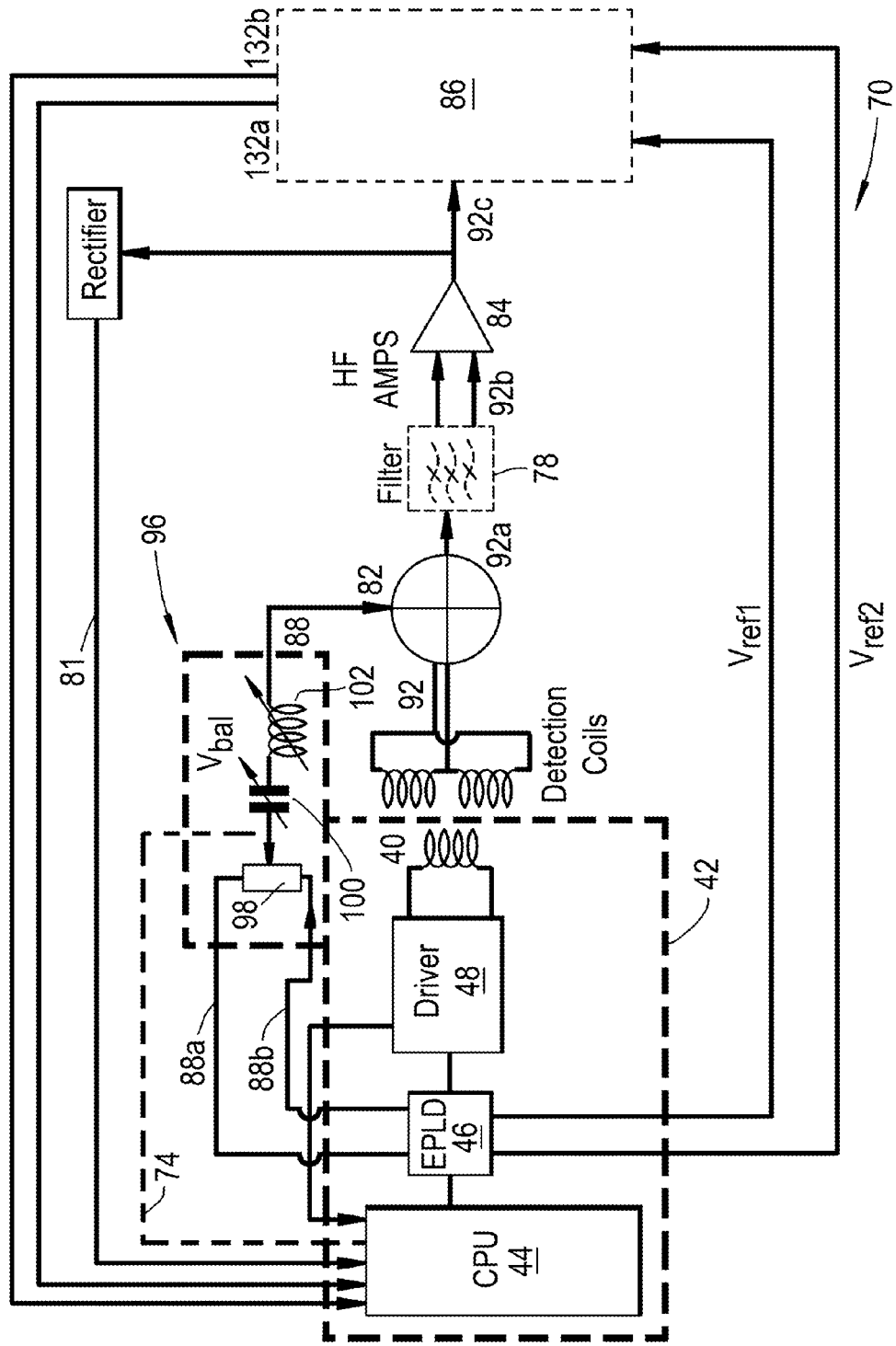
FIG. 9 is a circuit diagram showing means to generate and adjust an adjustable balance signal to combine with the output signal of the coil system according to a second embodiment of the present invention.

In an alternative embodiment of the present invention, the adjustable balance signal based on the drive signal can be adjusted/varied by controlling a tuning circuit 96 (R (resistance), L (inductor) and/or C (capacitor)) either connected in series or parallel commonly known in the art. As with the arrangement shown in FIG. 8, the adjustable balance signal 88 is based on the drive signal which is generated by exciting a crystal oscillator to generate a signal (see line 88(*a* and *b*) in FIG. 9) at the required frequency which is then fed into the tuning circuit 96. In FIG. 9 which shows the alternative arrangement of the drive circuit, the tuning circuit 96 which comprises a potentiometer 98, inductor 102 and the capacitor 100 are connected in series. The potentiometer 98 may be used to vary the amplitude of the adjustable balance signal and the capacitor/inductor 100, 102 may be used to vary the phase angle of the adjustable balance signal 88. As with the previous embodiment, using a digital potentiometer, digital capacitor and digital inductor enables their respective resistance, capacitance and inductance to be varied largely by software using the CPU 44 over the line 74. Alternatively, any one of the combination of the potentiometer and the capacitor or potentiometer and inductor can be used. The whole process of determining the balance state of the coil system is repeated for each operational frequency as discussed above whereby the output signal 92 from the detection coils is combined with the adjustable balance signal 88 in the voltage adder 82 to generate a combined output signal 92*a*. Following measurement of the combined output signal at a given frequency, any imbalance in the coil system is fed to the CPU via a feedback loop 81 which in turn varies the adjustable balance signal by varying the potentiometer and/or capacitor and/or inductance via the line 74 in order to create an adjustable balance signal 88 to effectively balance or nullify any imbalance in the output signal. The remaining features such as the low pass filter 78 behave similarly as discussed in the previous embodiment shown in FIG. 8*a*. More importantly, the position of the low pass filter can be after the voltage adder 82 following combination of the adjustable balance signal and the output signal. Alternatively, the adjustable balance signal 88 and the output signal can each be individually filtered by low pass filters prior to being combined by the voltage adder 82. Since it is inherent that the signal in the capacitor or the inductor respectively leads or lags behind the signal in the potentiometer by 90°, this will only allow the phase angle adjustments of the adjustable balance signal to be varied between +/−90° which may not cover the full range necessary to nullify the output signal from the detection coils. Again, as discussed in the first embodiment of the present invention, the EPLD coupled to the CPU establishes two reference signals Vref1 and Vref2 which are input into detection circuitry 86 shown as a dashed box. Further detail of the detection circuitry 86 is discussed later.

Figure 10:
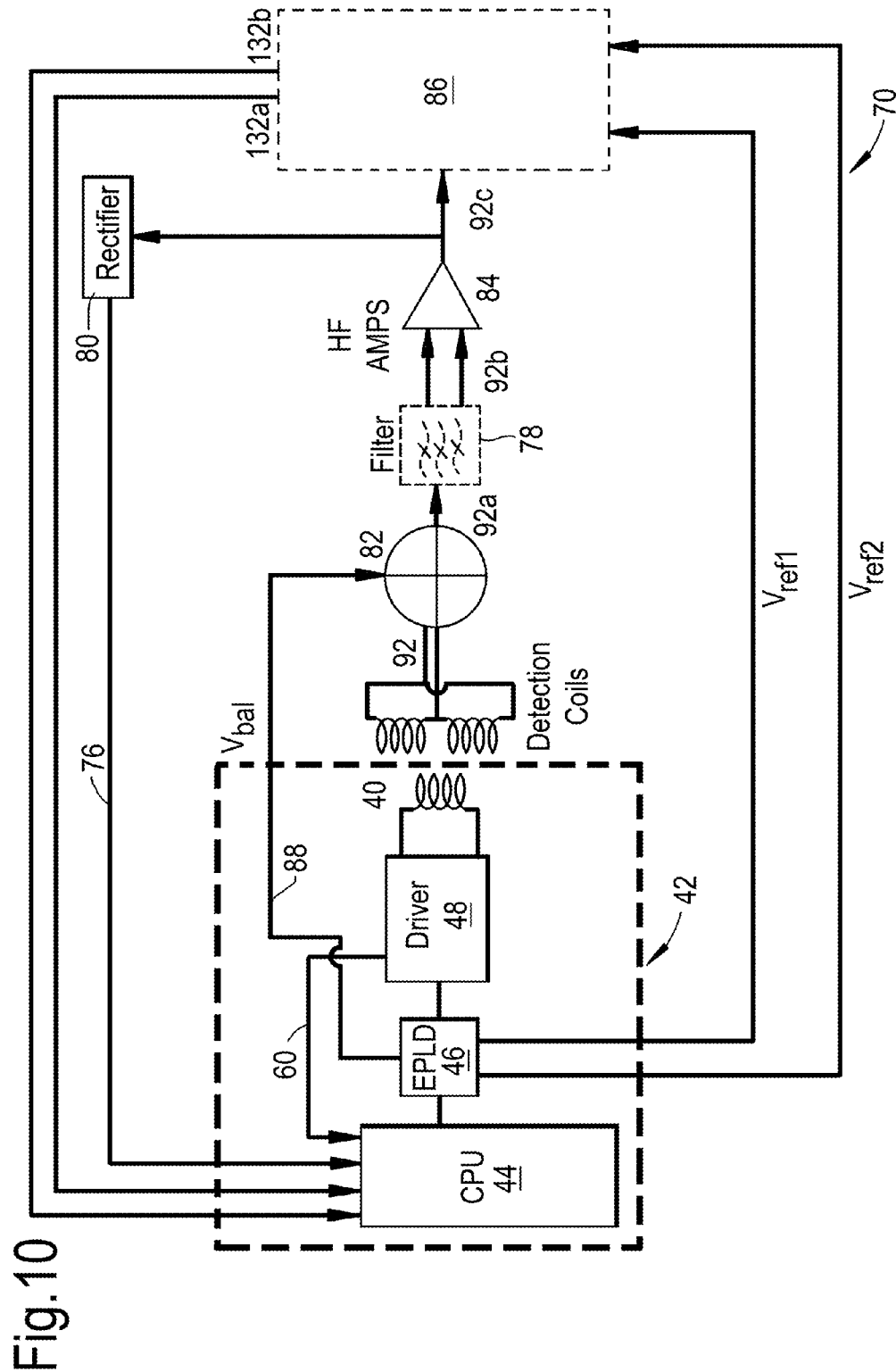
FIG. 10 is a circuit diagram showing means to generate and adjust an adjustable balance signal to combine with the output signal of the coil system according to a third embodiment of the present invention.

In a yet further alternative embodiment of the present invention and illustrated in the driver circuit 42 arrangement shown in FIG. 10, using a suitable driver software, the CPU 44 coupled to the EPLD 46 itself can be used to generate and vary the adjustable balance signal 88 so as to effectively nullify any imbalance in the detection coils. For example, the CPU 44 can be programmed to select a drive map stored in the EPLD or in the CPU itself to control the clock oscillator of the EPLD 46 to generate a signal 88 at an appropriate frequency. The amplitude and/or phase angle of the adjustable balance signal is varied by the CPU such that when combined with the output signal 92 in the voltage adder 82 any imbalance in the detection coils is effectively nullified. Sophisticated EPLD such as a FPGA, allows more flexibility over traditional programmable logic devices, so allowing the CPU to establish an adjustable balance signal of varying amplitude and phase angle at any given frequency. Again as with the previous embodiments, following amplification by the amplifier 84, the combined output signal 92*c* is measured at a given frequency and any imbalance in the coil system is fed to the CPU via a feedback loop 81 which in turn varies the adjustable balance signal in order to create an adjustable balance signal 88 to effectively balance or nullify any imbalance in the output signal.

Other means commonly known in the art to generate and adjust the phase and amplitude of a signal at one or more frequencies can be used as the adjustable balance signal. Examples include the use of a heterodyne, synthesiser, tuning circuits, digitally controlled crystal oscillators etc. The ability of modern CPUs to run at high clock speeds, e.g. in excess of 66 MHz, and with suitable driver software may even allow the adjustable balance signal to be primarily based on the clock speed of a modern CPU. Likewise, the frequency at which the drive coil is driven in the present invention is not restricted to a plurality of switches as taught in WO 2006/087510 (Spectrum Inspection Systems Ltd) and the frequency of operation of the drive coil can be provided by other means. For example, the drive coil can be driven by a tuned circuit as found in traditional metal detectors (see WO 02/25318 (Safeline Limited). Alternatively, the drive coil can be driven by any suitable digitally controlled oscillator or a synthesiser or even derived from the clock speed of the CPU. Equally, it is not necessary that the adjustable balance signal be derived from the drive signal used to drive the drive coil but a separate independent signal from another source whose amplitude and phase can be varied could be used. In all cases the frequency of the adjustable balance signal would need to be adjusted so that it is the same as the frequency of the drive signal. In conjunction with the CPU and at a given frequency, the amplitude and phase angle of the independent adjustable balance signal can be varied so that any detected imbalance in the coil system can be effectively nullified or reduced below a predetermined threshold value.

Figure 11A:
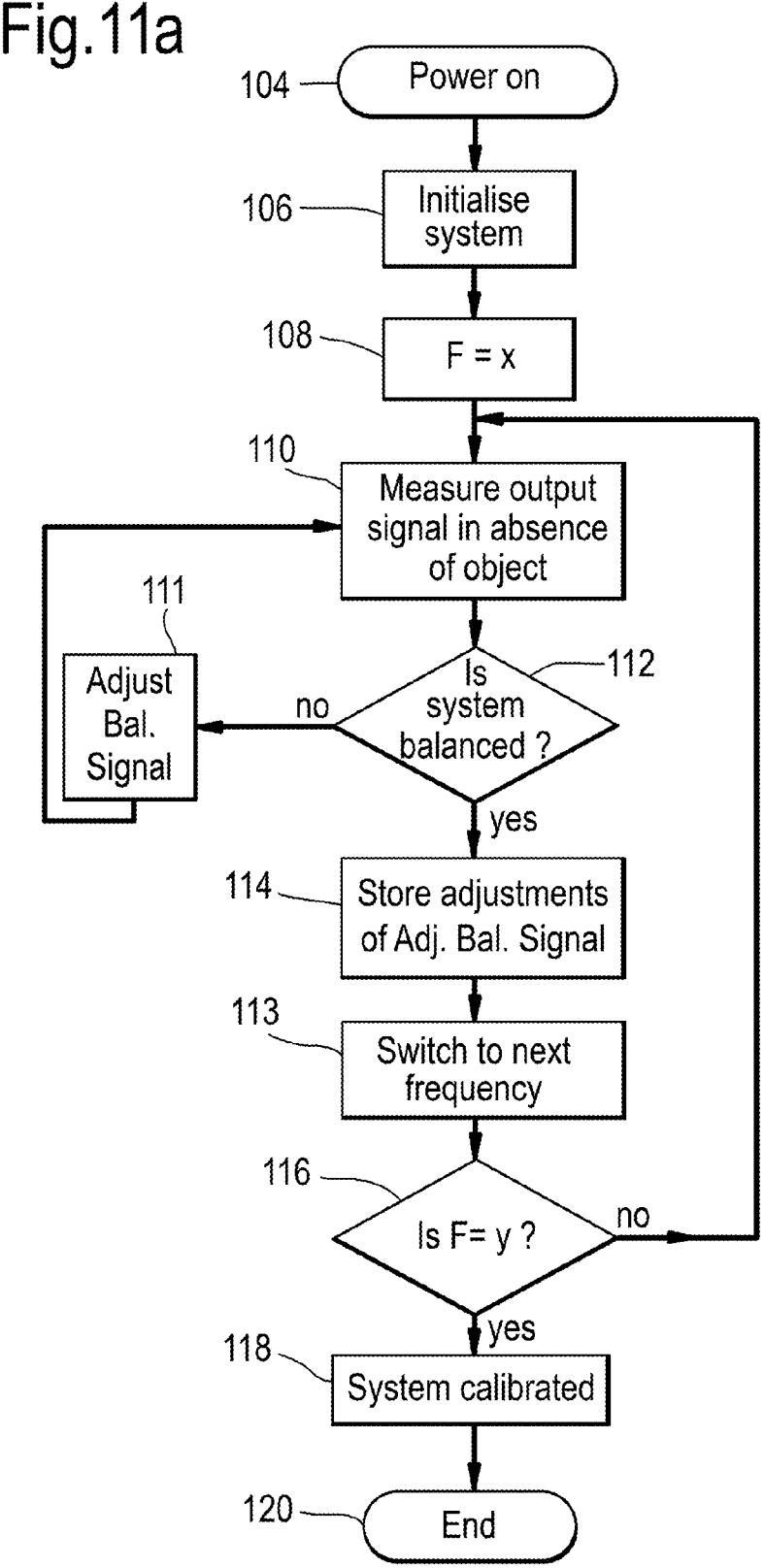
FIG. 11a is a flowchart showing the sequence of steps to calibrate the balance of the detector coil system according to an embodiment of the present invention.

FIG. 11 is a flowchart showing the sequence of steps used to nullify the output signal of the detection coils by the adjustable balance signal according to an embodiment of the present invention. The process described in the flowchart shown in FIG. 11a is usually carried out at the factory site prior to being shipped out to the customer's site, i.e. on first manufacture. However, the process may be repeated at the customer's site to cater for any imbalance of the coils due to the movement of the coils during transportation or movement of the metal detector or over a period of time of use at the customer's site, e.g. as a matter of routine procedure. During an initial start-up 104 of the metal detector, the system first initializes 106. This could involve resetting its internal memory from previous calibration set-ups or retrieving calibration information from its memory. In the absence of an object in the detector, the system then automatically scans across the range of frequencies operated by the metal detector from F=x to F=y and for each frequency the CPU measures the output signal 110 as described above. For example, the frequency of the drive signal can varied in successive steps, e.g. 10 Hz. If the CPU notices that the signal is in a balanced state 112, which for a perfectly balanced system would read zero, the CPU moves to the next frequency in the range 113. However, if the CPU realizes that the system is not in a balanced state, i.e. that the output signal is not zero, the CPU adjusts (step 111) the adjustable balance signal. This could be done incrementally. For example in the first embodiment of the present invention as shown in FIG. 8a, the CPU instructs the potentiometers, to incrementally adjust the balance signal and each time the potentiometers are adjusted the output signal is measured to determine if it has reached below a predetermined compensated value. Alternatively an additional step (not shown in FIG. 11a) can be added prior to step 110, whereby at a given frequency the system begins by applying a known adjustable balance signal to the output signal in absence of an object in the detector. For example, in the first embodiment of the present invention, applying a known adjustable balance signal can be derived by positioning the wiper of the potentiometers at a predetermined location on the resistive element forming the potentiometer, e.g. by centring the potentiometers. If the CPU notices that the signal is in a balanced state 112, which for a perfectly balanced system would read zero, the CPU moves to the next frequency in the range 113 and the process of applying a known adjustable balance signal to the output signal as described above is repeated for the next frequency. However, if the CPU realizes that the system is not in a balanced state, i.e. that the output signal is not zero, the CPU adjusts (step 111) the adjustable balance signal, e.g. in this example by adjusting the potentiometers until the adjustable balance signal effectively balances the output signal. Once, the output signal has reached a value below a threshold value, the adjustments are then stored in a database 114. This represents the adjustments needed to nullify the output signal at that given frequency of operation.

In some cases, where the output signal from the detection coils and associated circuitry, e.g. high frequency amplifier is fluctuating during each measurement of the output signal, a time delay can be incorporated between each measurement to allow the signal to stabilize. Preferably, the system calibrates the output signal at each frequency during the initial start-up of the detector. This is so that the time delay involved during an initial 'warming-up' of the metal detector, which in some cases can take over 20 minutes, would allow sufficient time for the signal to stabilize during each calibration measurement.

Once the output signal nullifying balance signal has been stored, the CPU moves to the next operating frequency. This process is repeated 116 for the other frequencies operated by the metal detector. A table is eventually built up showing the adjustments made to the adjustable balance signal at each corresponding frequency. In use for contamination detection, for each given frequency, the system retrieves the stored adjustments, e.g. from the database, so as to generate the necessary adjustable balance signal to balance the signal attributed to the imbalance of the detection coil system. In the case of the first embodiment of the present invention, for example, a table is built up showing the adjustments of the potentiometers (Pot 1 and Pot 2) at one or more successive frequencies. In practice, the CPU in dependence upon the information stored in the look-up table controls the operation of the digital potentiometers. This step can be carried out during or immediately after taking each reading of the output signal or can be carried out at the end when all measurements of the product to be tested, for the range of possible frequencies, has been determined.

The process described in the flowchart shown in FIG. 11a may be carried out using any computer having a suitable processor. Equally, the system may additionally use fuzzy logic to periodically measure the output signal for any given frequency in the absence of any object and continually update the database with the adjustment necessary to balance the system, i.e. the system continually learns to balance the output signal to provide a balanced system. The processor could be implemented using other conventional means such as a PROM, EPROM or dedicated electronic circuitry.

To re-balance the system, according to the present invention software or the like is preferably used to automatically re-configure the detector. For the case of the mechanical balance set in a resin, this removes the need to break the resin in order to allow the bent loop or coil to freely move again. Moreover, the above calibration steps shown in the flowchart of FIG. 11a may be used in combination with or conjunction to any mechanical balance 25 described above. For instance, for any large imbalance in the output signal such as in excess of 40% of the detection range, the mechanical balance may be used in preference to software techniques, since this easily provides crude adjustments to the signal. For very fine adjustments to the detection coil system, software or electronic methods may be used as described in the flowchart in FIG. 11a.

Figure 1:
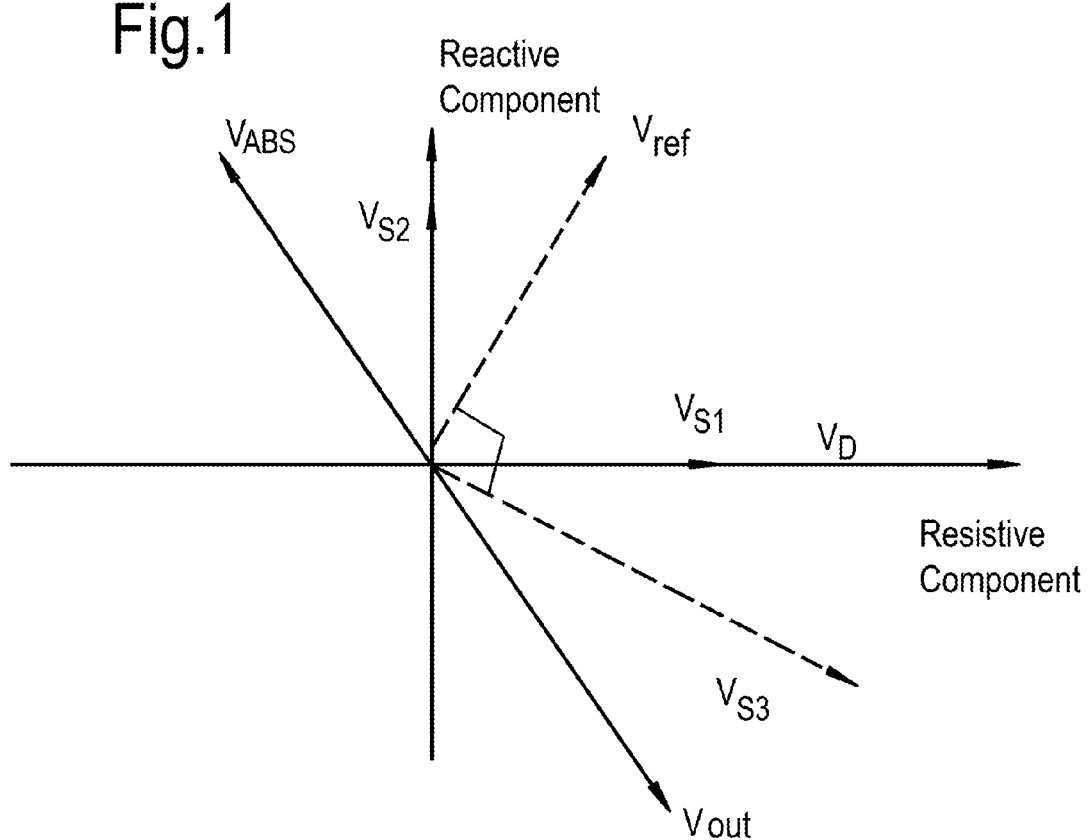
FIG. 1 is a vector phase diagram depicting the relative phase and amplitude of the drive signal and output signal of a metal detector.
Figure 2:
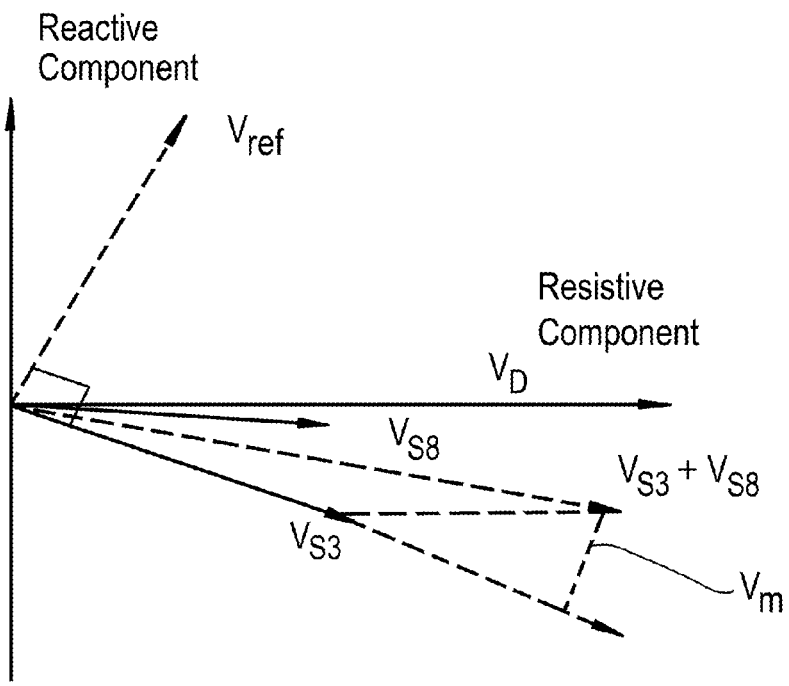
FIG. 2 is a vector phase diagram depicting the relative phase and amplitude of the output signal as a result of a metal contaminant.
Figure 12:
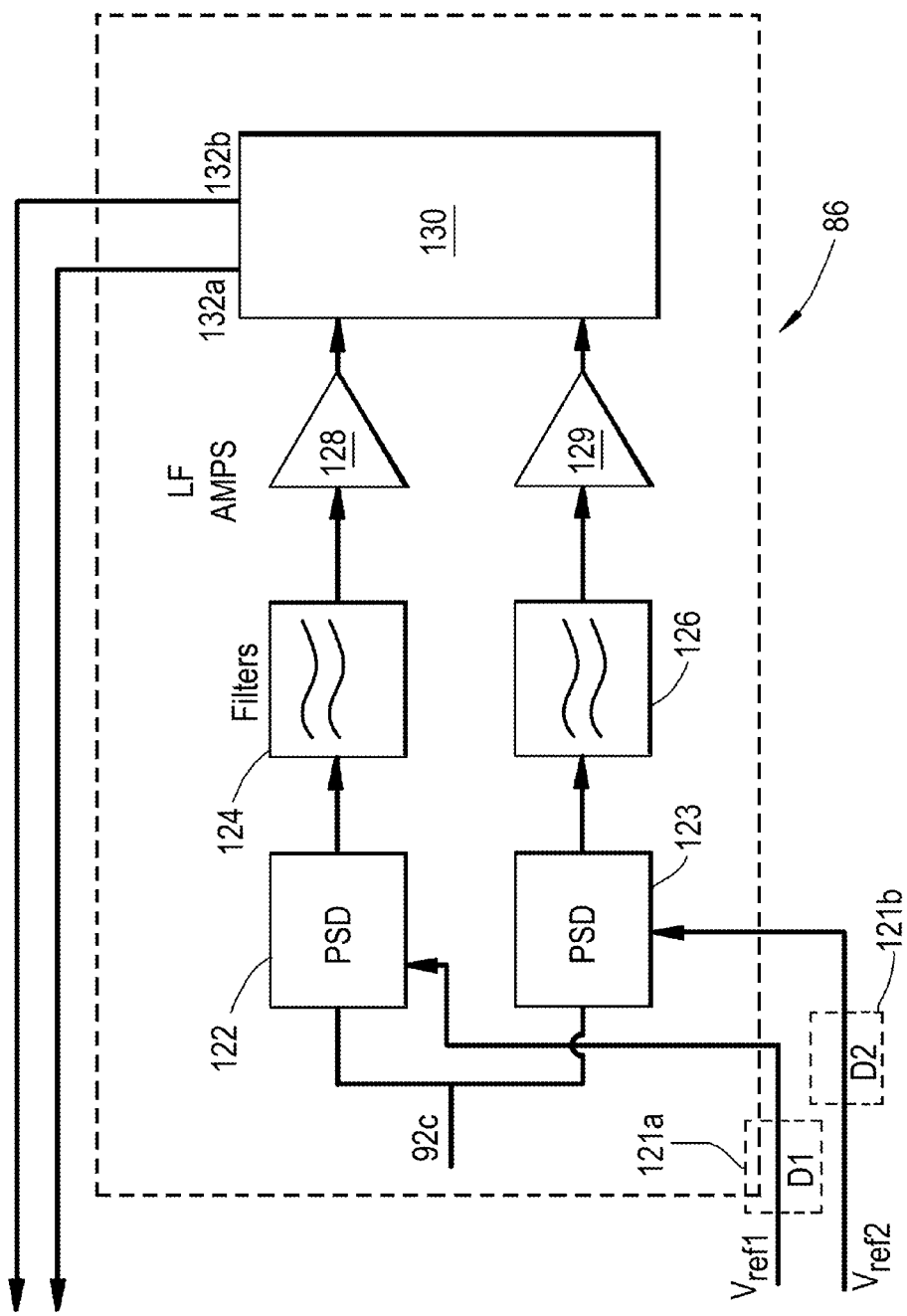
FIG. 12 is a circuit diagram of a portion of the detection circuitry according to an embodiment of the present invention.

As discussed above with reference to the vector diagram shown in FIG. 1, the interaction of a product under investigation between the detection coil system produces two signal components, known as the resistive and reactive signals, which tell the detector about the interaction of the product with the magnetic field. Largely conductive products such as copper or stainless will generate an output signal having largely a resistive component. On the other hand, due to losses in the material, the component of the output signal from a poor conductor but perfect or near perfect magnetic material such as ferrite material will substantially be in phase quadrature with the resistive component (i.e. reactive component). In an ideal situation where the resistive component is in phase with the drive signal, then the signal from ferrite will, therefore, be in phase quadrature with the drive signal. The output signals from the receiver coils will vary depending upon how conductive the product is. For instance, different types of products will interact differently with the magnetic field, each product having a resistive component and a reactive component and therefore, a characteristic phase angle. The phase angle between the reactive component and the resistive component of the output signal is effectively a "signature" for that particular product under investigation. The detection circuitry 86 (see FIG. 12) represented by the dashed box in FIGS. 8, 9 and 10 and the components associated with the detection circuitry such as phase sensitive detectors 122, 123, low pass filters 124, 126, amplifiers 128, 129 and level detector 130 may be as described in WO 2006/087510 (Spectrum Inspection Systems Ltd), whereby the EPLD 46 coupled to the CPU 44 establishes two reference signals Vref1 and Vref2 that are input into phase sensitive detectors 122, 123 respectively, together with the output 92 of the high frequency amplifier 84. The reference signals Vref1 and Vref2 are derived from the drive signal and therefore, are at the same frequency as the drive signal. In an ideal world, the phase angles of the reference signals, $Vref_1$ and $Vref_2$, are adjusted so that one of the reference signals, e.g. $Vref_1$ is in phase with the drive signal (resistive component) and the other reference signal, e.g. $Vref_2$, is in phase quadrature (90°) with the drive signal (reactive component).

When these are respectively input into the phase sensitive detectors, 122, 123 together with the output signal 92c as a result of the interaction of the product with the magnetic field, the phase sensitive detectors compares the reference signals, $Vref_1$, $Vref_2$ with the output signal and thereby, one of the phase sensitive detectors selects a component of the output signal that is in phase with the drive signal, denoted the P' signal and the other phase sensitive detector selects the component of the output signal that is in phase quadrature with the drive signal, denoted the Q' signal. For example, the P' signal represents the measured 'resistive' component of the output signal and the Q' signal represents the measured 'reactive' component of the output signal. This is in contrast to the P-signal and Q signal discussed above that is derived directly from the drive signal and so has a component that is in phase with the drive signal and a component in phase quadrature with the drive signal. This is not to say that the output signal can have a P' component that is in phase with the drive signal and a Q' component that is in phase quadrature with the drive signal, i.e. the component P and P' are in phase and the component Q and Q' are in phase. Where the P' signal is in phase with the drive signal and the Q' signal is in phase quadrature with the drive signal then when a perfectly magnetic material such as ferrite or a ferrite wand is passed between the receivers coils, one would expect a relatively weak or no P' signal indicating a weak conductive material component and a strong Q' signal indicating a strong magnetic material. In reality, this is not exactly the case and a perfectly magnetic material such as ferrite exhibits both a reactive component and a notable resistive component resulting in a slight shift in phase angle from the drive signal. This shift in phase angle can be attributed to the presence of noise in the detection systems, and can be attributed to the delay in monitoring or recording or processing the output signal from the receiver coils. During the interaction of the product with the magnetic field between the receiver coils, there is a slight delay in the system picking up the signal. In circumstances where the product is a dry product (no electrical conductivity), such as a hard frozen product, a small phase angle is generated. This delay could be due to the delay as a result of the interaction of the changing magnetic field with the product under investigation and the subsequent detection of the signal in the receiver coils by the detection electronics (e.g. phase sensitive detectors). This delay is usually characteristic of a particular metal detector. The phase angle θ of the output signal calculated from the measured, P' component and the quadrature, Q', component of the output signal (tan θ=P'/Q') is characteristic of the type of product under investigation. Different types of products will generate a different phase angle, θ. Without compensating for this delay in the output signal, products such as dry products which exhibit little or no electrical conductivity may result in a notable signal being detected by the detection circuitry and thus, an undesirable phase angle shift, δθ, from the 'true' phase angle that is characteristic of the product under investigation. In order to compensate for this delay, a delay factor is introduced in the reference signals, $V_{ref1}$ and/or $V_{ref2}$, so that during testing of products under investigation, the output signal is corrected for this phase angle change, δθ.

Figure 13A:
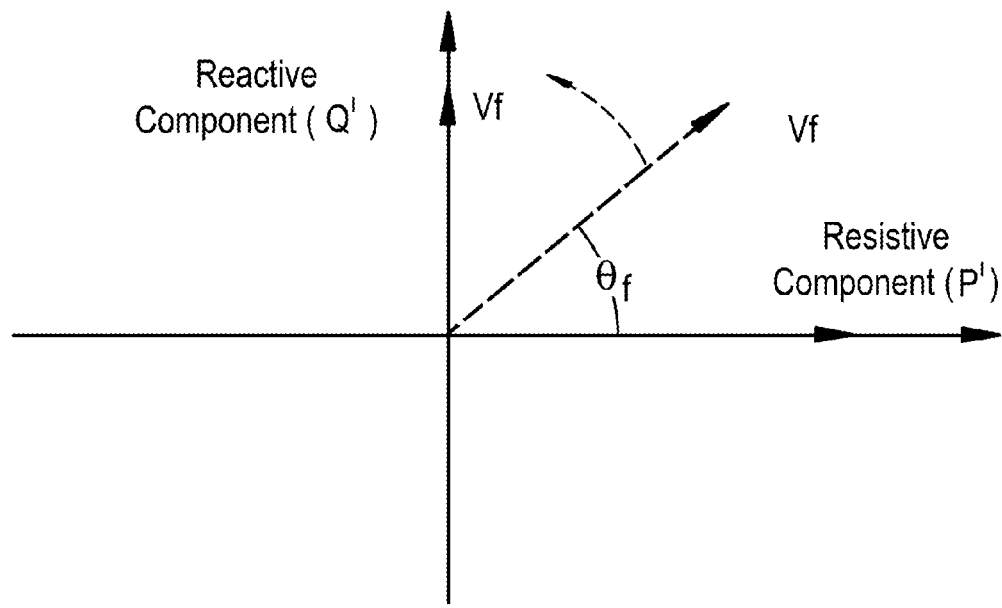
FIG. 13a is a vector diagram depicting the phase relationship between the output signal as a result of the interaction of ferrite.

To measure this delay factor, the reference signals, $V_{ref1}$ and/or $V_{ref2}$ are adjusted when a ferrite wand is passed between the detection coils at a given frequency. The reference signals, Vref1 and/or Vref2, are substantially in phase quadrature with respect to each other, so as to represent the reactive component of the output signal and the resistive component of the output signal (to mimic the reactive component being in phase quadrature with respect to the resistive component). As ferrite is considered to be a perfectly magnetic material, then in theory the output signal from the detection coils will primarily be reactive, i.e. show a strong Q'-signal. The reference signals, $V_{ref1}$ and/or $V_{ref2}$, can then be adjusted so as to discriminate any generated P'-signals leaving a purely Q'-signal as one would expect with ferrite. This can be demonstrated in the vector diagram shown in FIG. 13a. The vector, $V_f$ represents the output signal as a result of the interaction of ferrite with the magnetic field between the detection coils having a P' component and a Q' component. The output signal $V_f$ is in phase relationship with the resistive component by an angle, $θ_f$. To discriminate the P'-component of the output signal, the reference signal is adjusted so as to effectively make the output signal, $V_f$, the quadrature component, i.e. the Q'-component. The reference signals are adjusted so that when the reference signal and the output signal are compared by the phase sensitive detectors, 122, 123, the P'-component as a result of the interaction of ferrite with the magnetic field will substantially produce a zero output and the output signal primarily becomes the Q'-signal. By establishing a maximum and minimum relationship between the Q' and P' components of the output signal in the presence of ferrite, the system can readily identify that the detection coils are compensated for any noise or delays in the detection system, i.e. a condition is reached whereby the Q' component represents the 'true' reactive component of the output signal. When this condition is reached, the adjustments made to the reference signals at a given frequency, Vref1 and Vref2, are stored in a look-up table or database for later retrieval. Alternatively, the system can calculate and compare the difference between the Q' component and the P' component of the output signal such that the system is calibrated when the difference between the Q' component and the P' component reaches a maximum value. For example, maximum value is reached by equating one of the components (Q' or P') to zero in the presence of ferrite.

The relationship between the reference signals, Vref1 and Vref2, and the output signal can be explained by equation (1) below. The output, Vo1, of the phase sensitive detectors (PSD), 122, 123, is given by:—

$$Vo1 = K \cdot Vin \cos θ \quad (1)$$

Where K is a constant,
  Vin is the input signal of the PSD at the output of the HF amplifier 84 (i.e. the output signal), and
  A is the phase difference between Vin and Vref1 or Vref2.
In order to compensate out or discriminate signals that are 90° out of phase with the respect the reactive signal, the reference signals, Vref1 and Vref2, are set so that they are substantially in phase quadrature with respect to each other. Therefore, when the phase angle between the reference signal, either, Vref1 or Vref2, and the output signal, Vin, is 90°, Cos 90° is zero and therefore that component of the output signal has been discriminated or compensated out since according to equation 1, Vo is also zero. In the presence of ferrite, when the output of one of the phase sensitive detectors is adjusted to read substantially zero, then theoretically the output from the other phase sensitive detector should be at a maximum since this represents the reactive component of the output signal. This is because the reactive component is in phase quadrature with the resistive component and since the reference signals, Vref1 and Vref2, are set in phase quadrature with respect to each other, then theoretically, the reading from the other PSD will be at a maximum. It is this relationship between the PSDs, 122,123, in the presence of ferrite that enables the user to determine whether the detection system is in a compensated state.

It should be noted, that the components of the output signal P' and Q' are not necessarily in-phase and in-phase quadrature with the drive signal respectively and can be at any arbitrary angle. The phase angle between the P' and Q' component of the output signal is primarily dictated by the phase angles of the reference signals, Vref1 and Vref2 with respect to the drive signal. Thus, the reference signals, Vref1 and Vref2, although can be derived from the drive signal can be adjusted at any arbitrary phase angle with respect to the drive signal. This is made possible by the use of sophisticated logic circuits (EPLD) as will be discussed below. For example, if one reference signal, Vref1, is set at 45° with respect to the drive signal and the other reference signal, Vref2, is set in phase quadrature to this, i.e. at 135° with respect to the drive signal so that they are 90° apart, then when combined with the output signal of a product, Vref1 picks out the signal 45° in phase with the drive signal and Vref2 picks out the signal 135° with the drive signal. If the product under investigation is ferrite and for explanation sake, the output signal from ferrite lies at a phase angle of 45° with respect to the drive signal, then Vref2 effectively discriminates the output signal from ferrite (since A=90°) and thus, Vref1 dominates the output signal in other phase sensitive detector since Vref1 and the output signal are in phase. As ferrite represents the perfect magnetic condition, then the combination of Vref1 and the output signal from ferrite would be considered to lie on the reactive axis and that the signal in phase quadrature to that would be the resistive component. This can be demonstrated in FIG. 13a by effectively rotating the vector, Vf, by a suitable correction angle (90°−θf) so that the output signal, $V_f$, substantially lies on the Q'-axis (reactive axis). By compensating this P'-signal out, the metal detector is very stable and achieves best performance for future testing. The reference signals, Vref1 and Vref2, are varied or adjusted together whilst maintaining the phase angle difference between them constant. Since the reactive component is in phase quadrature with the resistive component, the phase angle between Vref1 and Vref2 is usually set at substantially 90° so that the output from one of the phase sensitive detectors represents the reactive component of the output signal and the other phase sensitive detector represents the resistive component of the output signal.

However, the phase angle between the reference signals, Vref1 and Vref2, may not be restricted to being in phase quadrature with respect to each other, since it is perfectly permissible to set the system to detect an output signal from the first phase sensitive detector (PSD) to be equal to or below a first predetermined threshold value and the output signal from the second phase sensitive detector (PSD) to be equal to or above a second predetermined threshold value, the threshold value being determined largely by Cos A where A varies between 0° to 180°. Thus, the phase angle of the reference, Vref1 or Vref2, may not necessarily be in phase quadrature with the resistive component of ferrite, it can be at some other angle such that when the output signal from ferrite and the reference signal are compared in the phase sensitive detector, the output from the phase sensitive detector is below or equal to a first predetermined threshold value. Likewise, the other reference signal may not be in-phase with the reactive signal but at some other angle such that the output from the second phase detector is above or equal to a second predetermined threshold value. The first predetermined threshold value is an indication of the resistive component of ferrite and the second predetermined threshold value is an indication of the reactive component of ferrite. For example, whilst to discriminate the resistive component of the output signal from ferrite, it is necessary that the reference signal is adjusted so that the reference signal is in phase quadrature with the output signal from ferrite, by adjusting the reference signal, Vref1 or Vref2, such that it is slightly less or greater than 90°, will result in an output other than substantially zero, e.g. Cos 89°=0.017. Likewise, the other reference signal, Vref2 or Vref1, can be adjusted so that it is not exactly in phase with the output signal from ferrite but at some other arbitrary phase angle such that a maximum value is reached when the output from the other PSD reaches above or equal to a second predetermined threshold other than 0°, e.g. Cos 5°=0.0996. Thus, the phase difference between the reference signals, Vref1 and Vref2, need not be exactly 90° apart but some other arbitrary predetermined phase angle so in order to generate a maximum threshold value from one reference signal, Vref1 or Vref2, and a minimum threshold value from the other reference signal, Vref2 or Vref1, in the presence of ferrite. The size of the first and the second predetermined threshold values will be dependent upon what is deemed acceptable to the user. For example, an acceptable calibration may be achieved in the presence of ferrite, when the phase angle is +/−5° from the reactive component and the resistive component of the output signal. Taking this range as an example, the phase angle between the reference signals can be varied between 95° and 85°.

In the particular embodiment, the EPLD (Electronic Programmable Logic Device) may be programmed (e.g. by software) to vary/adjust the reference signals, Vref1 and Vref2, by incorporating a delay factor (e.g. by adjusting the high speed counter or drift register), $D_1$ (121a) and $D_2$ (121b) respectively, to the reference signal, $V_{ref1}$, that represents the P'-signal and to the reference signal, $V_{ref2}$, that represents the quadrature component, i.e. Q'-signal. In yet another embodiment of the present invention, the reference signals, Vref1 and Vref2, can be varied or adjusted incrementally in sequential steps whilst maintaining their phase relationship between each other and at each adjustment of the reference signal, Vref1 and Vref2, the output from the phase sensitive detectors, 122, 123, are monitored to see if the output signal from ferrite is equal to or below a first predetermined threshold value in one of the directions of the output signal and above or equal to a second predetermined threshold value in the other direction of the output signal. Where the reference signals, Vref1 and Vref2, are in phase quadrature with respect to each other, then the output signal is compensated out or discriminated when the reference signal, Vref1 or Vref2, is in phase quadrature with the output signal, i.e. A=90°, Cos A=0 and conversely yield a maximum value when they are in-phase with the output signal respectively. Where the reference signals are based on the signal derived and controlled by the EPLD, then the EPLD can be digitally programmed to automatically vary the reference in sequential steps.

Figure 11B:
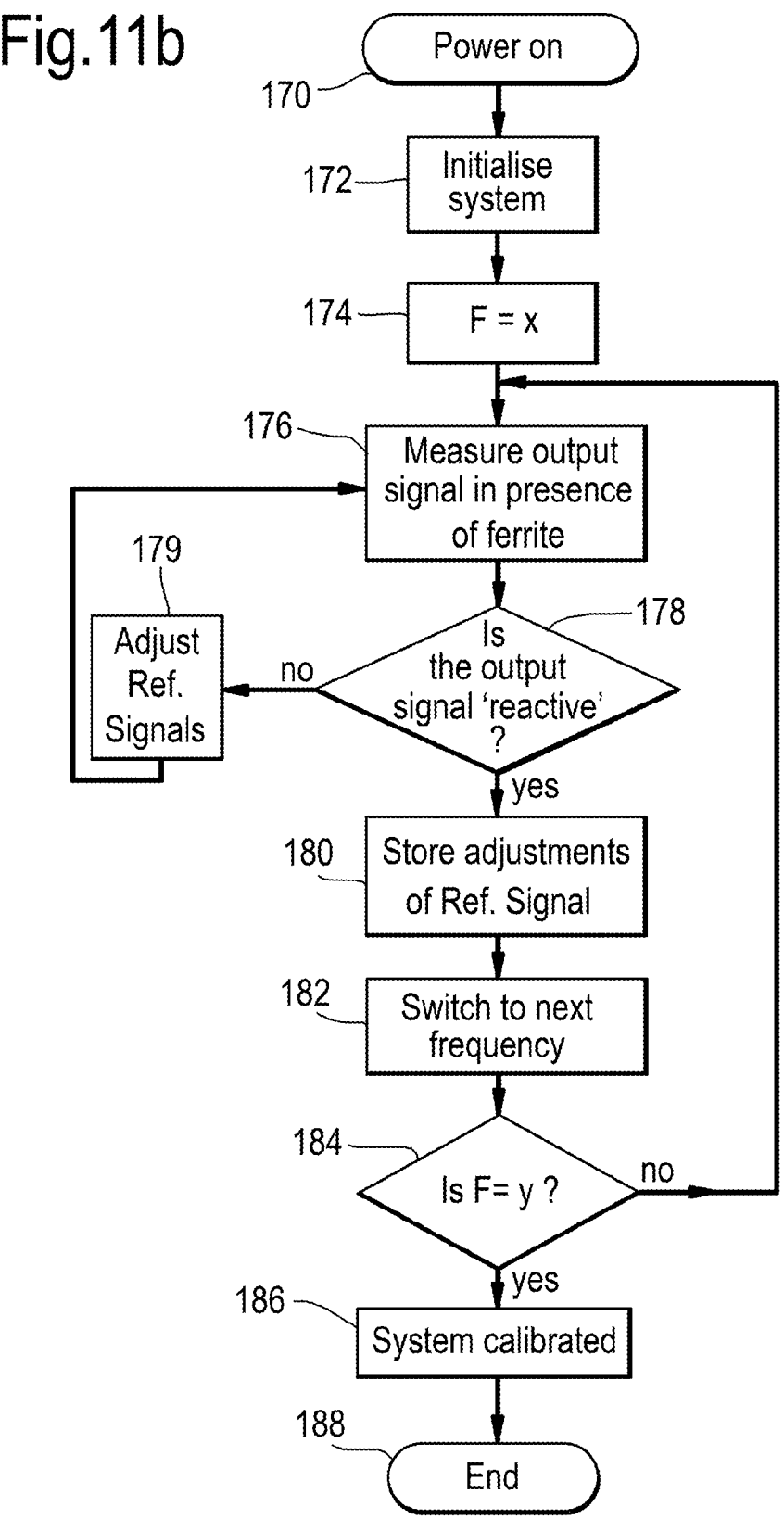
FIG. 11b is a flowchart showing the sequence of steps used to compensate the output signal of the detection coils for any noise according to an embodiment of the present invention.

Once calibrated for noise or delay in the system, the output signal from ferrite and $V_{ref1}$ and $V_{ref2}$ are compared by the phase sensitive detectors, 122, 123, respectively so as to select the "corrected" P'-signal (P" signal) and the "corrected" Q'-signal (Q" signal) by adjusting for this phase angle shift as a result of the delay in the detection electronics. In the case of the presence of ferrite, the corrected Q" signal will dominate the output signal with very little or no P" signal. The corrections made to the reference signals, $V_{ref}1$ and/or $V_{ref2}$, at a given frequency are stored electronically in a look-up or database for later retrieval whenever the metal detector is operating at that frequency. In the case of a variable frequency metal detector whereby the range of frequencies is provided by the operation of a plurality of switches, the corrections made to the reference signals, $V_{ref1}$ and/or $V_{ref2}$, to compensate for this delay factor is repeated at the different operating frequencies. A look-up table is eventually built up showing the corrections factors that need to be made to the reference signals, $V_{ref1}$ and/or $V_{ref2}$, at the different operating frequencies to compensate for this delay factor. As this delay is usually characteristic of a particular metal detector, providing for this calibration can be carried out at the factory site prior to being shipped out to the customer's site, i.e. on first manufacture. FIG. 11*b* is a flowchart showing the sequence of steps used to compensate the output signal for any noise or delay, according to an embodiment of the present invention. During an initial start-up 170 of the metal detector, the system first initializes 172. This could involve resetting its internal memory from previous calibration set-ups or retrieving calibration information from its memory. In the presence of ferrite between the detection signal, the system then automatically scans across the range of frequencies operated by the metal detector from F=x to F=y and for each frequency, the CPU measures the output signal 176 as described above. As with the auto-balance procedure described with reference to FIG. 11*a*, the frequency of the drive signal can be varied in successive steps. If the system notices that at a given frequency, the output signal from ferrite is not in the reactive region, i.e. both PSDs, 122, 123, produce a measurable output, then the reference signal is adjusted 179 such that the output signal is compensated out in one direction and the output signal is largely dominated in another direction (the true reactive direction). In other words, the reference signals are adjusted 179 so that a maximum and minimum relationship are established from the PSDs, 122, 123. This represents the true Q' component of the output signal, which is analogous to the reactive component and the true P' component of the output signal, which is analogous to the true resistive component. The adjustments made to the reference signals at that given frequency are then stored 180 in a look-up table or database for later retrieval. The CPU then moves onto the next frequency 184 in the range and the whole process is repeated.

Each time the metal detector is used to test products under investigation at a given frequency, the metal detector, more particularly the processor, automatically retrieves the appropriate correction factor from the look-up table to automatically adjust the reference signals, $V_{ref1}$ and/or $V_{ref2}$ so as to compensate for the delay in the detection system. Once the reference signals are adjusted for this delay, the output signal from products under investigation will have a P" component and a Q" component, i.e. (the corrected P' component and the corrected Q' component).

In addition to the delay in the interaction of the product under investigation and subsequent measurement of the output signal, there is also noise attributed to the movement of the coil system. The coil system is very sensitive to any slight movement such as vibration resulting in an undesirable noise signal in the detection coils. For dry products which exhibit no electrical conductivity, the system (microprocessor) will get confused as to whether the output signal is as a result of the interaction of the magnetic field with the dry product or attributed to noise, i.e. the system will find it difficult to separate the output signal from the product under investigation and that from noise alone. To compensate for this noise at given frequency, the reference signal is adjusted in the presence of ferrite between the detection coils since the interaction of ferrite with the magnetic field generates a signal closely resembling noise. One way to compensate for noise is by discriminating or compensating out the output signal from ferrite at a given frequency. In other words, the reference signal is adjusted so as to produce a signal which when compared with the output signal from ferrite in the phase sensitive detector effectively discriminates this signal, i.e. the signal from ferrite will be used as the fixed reference point. Thus, in the presence of dry products having little or no electrical conductivity, the output signal will be compensated for noise allowing the metal detector to work from a known fixed reference point. By compensating for any delays in the detection system discussed above will also compensate for any noise in the detection system. This is because the output signal from ferrite will be used as a fixed reference point.

This in combination with the auto-balance system discussed earlier provides for a very stable metal detector that achieves best performance. However, compensating for any noise or delays in the detection system can be independent of the calibration steps used to compensate for any imbalance in the output signal as discussed above. Moreover, the steps used to digitally compensate for the any delays or noise in the measurement of the output signal is not necessarily restricted to a variable frequency detector and can be applied to other traditional metal detector systems as an add-on facility so as to improve the accuracy of traditional metal detectors, e.g. used to upgrade traditional metal detector systems (e.g. based on a tuning circuit). In the particular embodiment, compensating for the noise or delays in the measurement of the output signal was described with reference to a variable frequency metal detector.

Figure 13B:
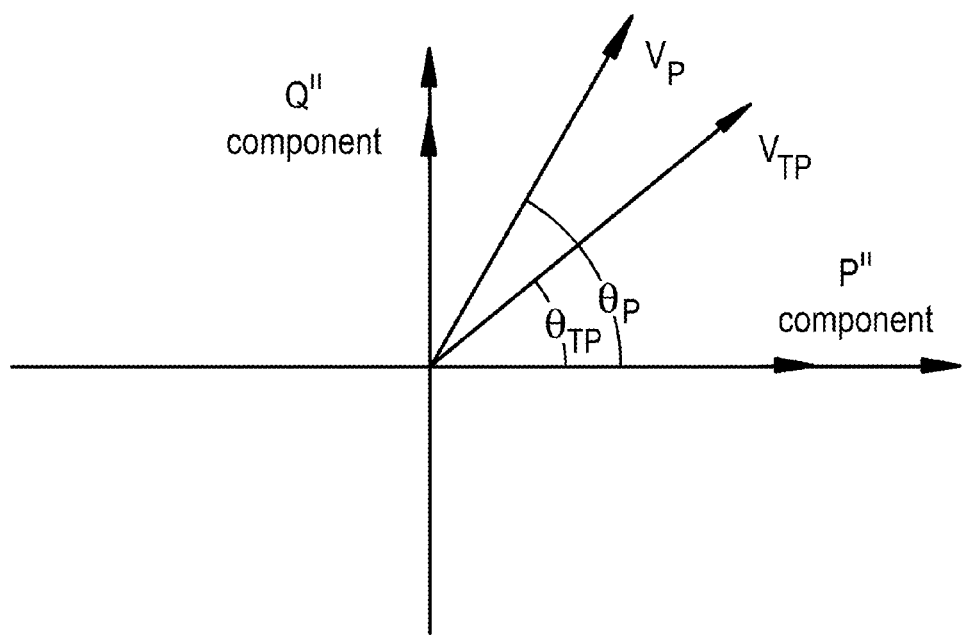
FIG. 13b is a vector diagram depicting the phase relationship between the output signal as a result of the interaction of a product containing a metal contaminant with a "clean" product.

Once the adjustments needed to be made to the reference signals have been established at a given frequency and stored in a look-up table or database, the metal detector is then ready to detect for any metal contaminants in products under investigation. There may be two separate look-up tables or databases to cater for the compensation in respect to noise or delays and any imbalance in the coil system. Populating the look-up table or database with the compensating values may be carried out at the factory site prior to being shipped out to the customer. In the absence to compensating for noise or delays, the output signal will have a P' component and a Q' component. The measurement of the P' and Q' values at given frequency in the foregoing description will be described with reference to the P" (corrected P' value) and Q" values (corrected Q' value) that has been compensated for the noise or delays and/or imbalance as discussed above. At a given frequency, the system retrieves the corrections that need to be made to the reference signals so that when combined with the output signal from the product under investigation in the phase sensitive detectors generates the corrected P" and Q" signals that has been compensated for any noise or delays in the system and/or imbalance in the coil system. The corrected P" and Q" values can be represented graphically by the vector diagram shown in FIG. 13b. The vector, Vp, represents the output signal at a given frequency as a result of the interaction of a product under investigation with the magnetic field between the detection coils having a P" component and a Q" component that have been corrected for any delay/noise in the system. By taking into account any delays or noise in the detection electronics, the output signal from ferrite will, therefore, largely result in a Q" signal and little or no P" signal.

The output signal Vp is in phase relationship with the drive signal by the angle, $\theta_P$. The output of each phase sensitive detector 122, 123 is passed through respective low pass filters 124, 126, whose outputs are amplified by low frequency amplifiers 128, 129 before passing to a level detector and alarm unit 130. The level detector 130 provides a feedback line 132 (a and b) to the central processor unit 44 in the form of the P" (132a) and Q" (132b) values. The unit 130 triggers an alarm if the signal from either of the low frequency amplifiers 128, 129 exceeds a predetermined threshold value.

The corrected P" and Q" values as a result of the interaction of the product with the magnetic field between the detection coils are characteristic of a particular product. Different product types will exhibit different P" and Q" values that is characteristic of a particular product type. Thus, the next procedure is calibration of the metal detector for a particular product and involves establishing the P" and Q" values of the product at a given frequency of operation. This usually involves the selection of the ideal operational frequency of the metal detector for a typical product under investigation depending upon the characteristics of the object, such as its level of electrical conductivity and magnetic permeability. This ensures that should a metal particle type and size be such that at a specific frequency, the phase angle of a component of this output signal due to the metal particle corresponds to the same phase angle of the output signal from the product alone, and thus is masked by the output signal of the product, then at the second frequency, the phase angle of the two components will change by different amounts, such that the signal from a metal contaminant will be distinguishable from that generated by the product alone. By switching between many frequencies, one frequency should provide substantially optimal sensitivity for any particular metal type, size and orientation. This is the product calibration stage and is usually done by manually switching through a range of different operating frequencies, e.g. depending upon the experience of the operator. Alternatively, the product calibration stage can be done automatically by sequentially scanning the product over a plurality of different frequencies in order to select an ideal frequency depending on its level of electrical conductivity and magnetic permeability for detecting metallic contaminants such that any metal particle in the product will be subject to scanning at different frequencies. By driving the coil by means of a plurality of switches as discussed above, the system allows a suitable frequency to be chosen from a wide range of frequencies.

Figure 14:
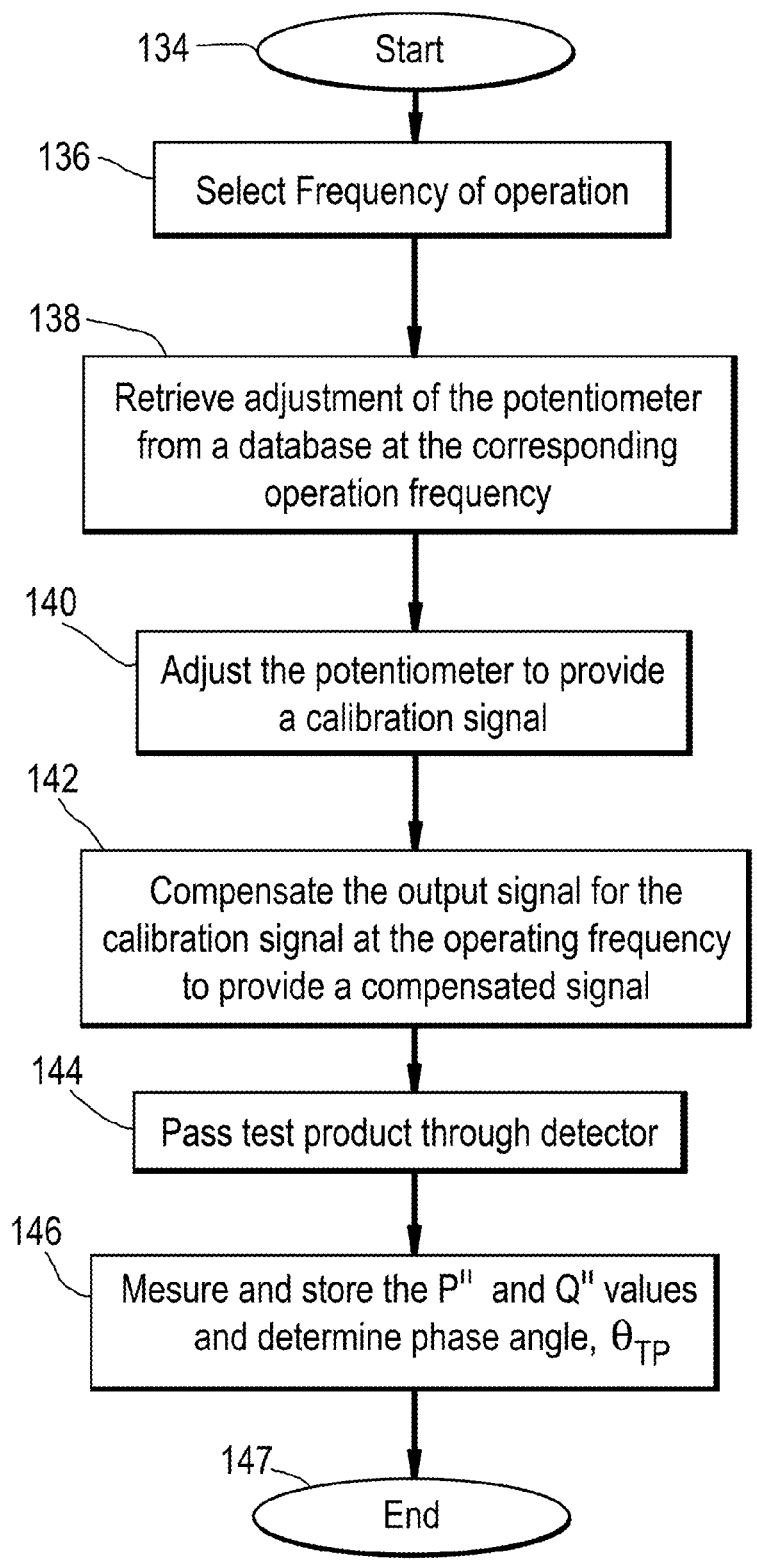
FIG. 14 is a flowchart showing the sequence of steps to calibrate the detector coil system according to a particular product type.

The flowchart in FIG. 14 shows an example of the sequence of steps used to calibrate any imbalance in the metal detector for a particular product type under investigation with reference to the potentiometers as shown in FIG. 8a. However, the sequence of steps shown in the flowchart in FIG. 14 is applicable to the other embodiments where the adjustable balance signal is varied by a tuning circuit or the EPLD. The first stage of the process involves the selection of the ideal frequency of operation of the metal detector for a particular product 136 under investigation. This is usually done manually depending upon the operator's experience but can be done automatically as described above. Once the frequency is selected, the processor then sets the metal detector to operate at that frequency. The system then searches the database and retrieves the stored adjustment of the potentiometer 138 from the earlier calibration process (see FIG. 11a) at the corresponding operating frequency. The potentiometer is then adjusted to provide an adjustable balance signal (step 140). In the case of the second and third embodiment of the present invention shown in FIGS. 9 and 10, the system retrieves the stored adjustments of the tuning circuit or selects an appropriate drive map from the EPLD respectively. The output signal is then compensated 142 by the adjustable balance signal so that any imbalance inherent in the detection coil system at that frequency is taken into consideration. Where in the absence of an object or 'dry products' in the detection coil, there are no changes in the measured output signal, i.e. the output signal is substantially equal to zero for a perfectly balanced system, no changes are made to the output signal during the testing phase. Thus the system of the present invention can also provide a dynamic calibration system whereby the output signal in the absence of any object is continually updated to take into consideration any imbalance in the detection coil system. In combination or independently to balancing any imbalance in the output signal at a given frequency, a secondary calibration can be performed between the steps 140 and 144 in FIG. 14 (not shown) to compensate for any noise or delays in recording/measuring the signal in the detection electronics as discussed above with reference to FIG. 11b. For ease of explanation, the measured P" and Q" values of the output signal are discussed when the output signal is compensated for any noise/delays and/or imbalance in the detection system, i.e. alone or together. At the given operating frequency of the metal detector, adjustments made to compensate for the noise or delays are retrieved from a database or look-up table. The reference signals, Vref1 and/or Vref2, are then adjusted to compensate for this delay as discussed above, such that the output signal in the presence of ferrite in one direction is equal to or below a first predetermined threshold value and the output signal in the other direction is equal to or above a second predetermined threshold value. Where the reference signals, Vref1 and Vref2 are in phase quadrature with respect to each other, then the output signal from ferrite will largely be dominated by a Q" component (reactive component) and a negligible P" component. This provides the 'true' P"-signal and 'true' Q"-signal. The look-up table or database for storing the adjustments to the reference signals can be stored in any storage device externally or within the metal detector and can be separate to the database for storing the adjustments needed to correct the imbalance in the system.

In step 144, a test product (with no contamination) is passed through the aperture of the detector 144 in order to establish the corrected P" and Q" values associated with that product type (step 146). In addition to the P" and Q" value, the phase angle, $\theta_{TP}$, can thus be determined through simple trigonometry (Tan $\theta_{TP}$=Q"/P") and stored in a database. This is the product calibration stage and is repeated when a different product type is placed on the product line.

Figure 15:
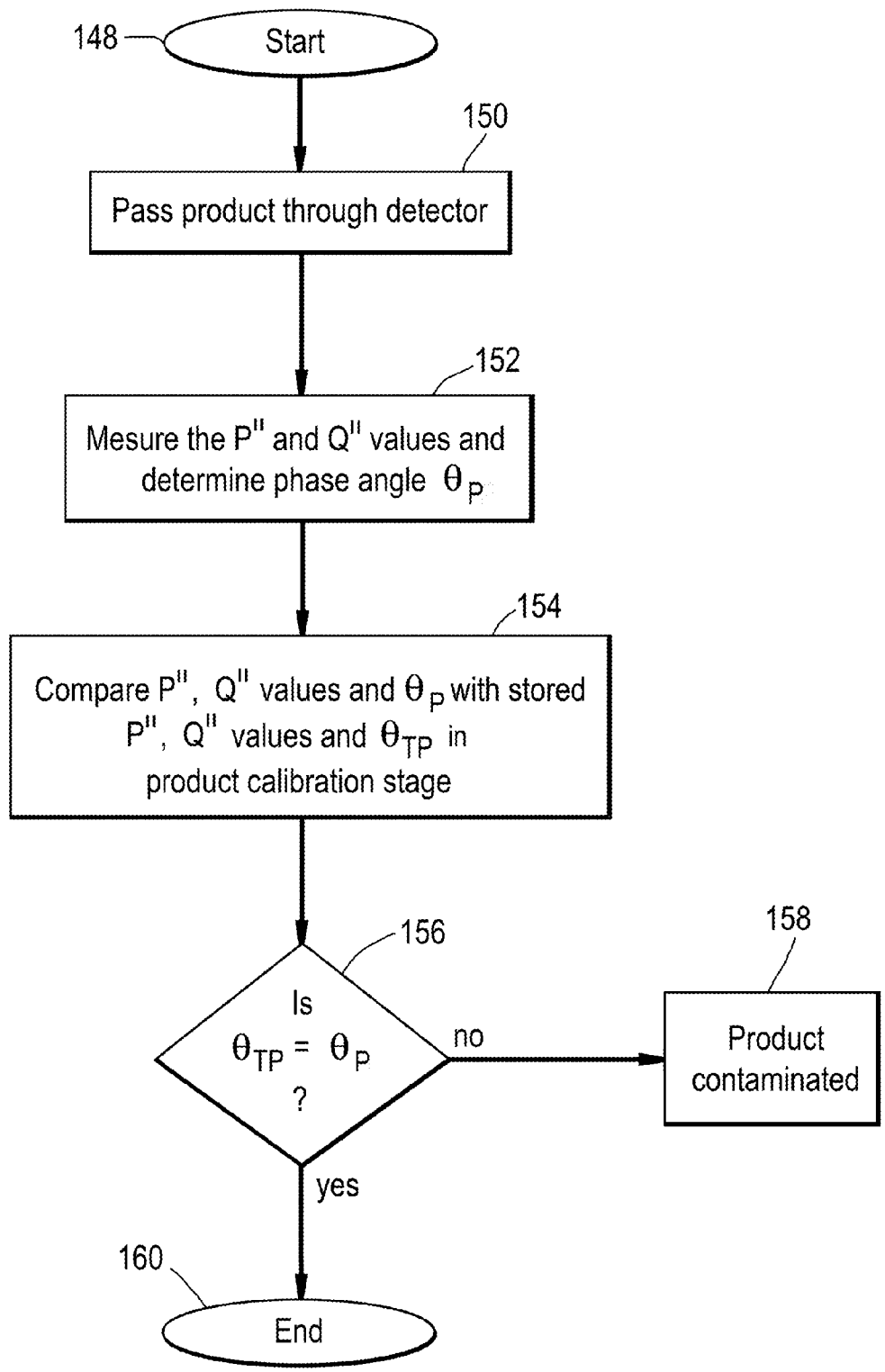
FIG. 15 is a flowchart showing the sequence of steps in the testing of products for metal contamination according to an embodiment of the present invention.

Once the metal detector is calibrated for any imbalance in the detection coils (FIG. 11a) and/or noise or delays as a result of delay and moving metal (FIG. 11b) and for a particular product type (FIG. 14), the metal detector is then ready to accept similar products to determine whether they contain any metallic contaminants. FIG. 15 shows the sequence of steps in the determination whether similar products used in the product calibration stage (FIG. 14) is contaminated or not. Initially the products are passed through the aperture of the metal detector 150. The corrected P''' and corrected Q''' values are measured to determine the phase angle, $\theta_P$, 152. The phase angle, $\theta_P$ is characteristics of that particular product type. The P''' and Q''' values are compared vectorially with the stored P''' and Q''' values associated with the "clean" test product in the earlier product calibration process 154 (FIG. 14). More specifically the phase angle, $\theta_P$, is compared with the stored phase angle, $\theta_{TP}$, associated with the clean test product. In the case, where the product is perfectly acceptable, i.e. contains no metal contamination, then the phase angle of the output signal associated with the product, $\theta_P$ is substantially the same as the stored phase angle associated with a clean test product, $\theta_{TP}$, i.e. the interactions with the magnetic fields are substantially the same. However, in the case where the product contains a metal contaminant, then the interactions of the magnetic field with the metal contaminant will be different with that of the product resulting in an output signal having a different phase angle to a normal clean product. Thus, the calculated phase angle $\theta_P$, determined from the measured P''' and Q''' values will be substantially different from the stored phase angle, $\theta_{TP}$, associated with a clean product. This can be represented vectorially in the diagram shown in FIG. 13b. The vector, $V_P$, representing the output signal through the interaction of the product containing a metal contaminant is shown to be at a different phase angle, $\theta_P$, from the test product, $\theta_{TP}$, indicating a metal contaminant.

In these situations, the microprocessor then looks to see if there are any phase angle changes as a result of a contaminant as opposed to when there is no contaminant in the product. Thus, if there is a measurable phase angle change of the output signal compared to a perfectly acceptable product, then this will trigger an alarm of the presence of a contaminant.

The sequence of steps for calibrating any imbalance and/or noise or delays in the system is not restricted to that shown in FIGS. 11, 11b and 14 and alternative methods to compensate the measured output signal with an adjustable balance signal and/or reference signal are applicable. For example, the detection coil system can be calibrated at the same time as when products are tested (e.g. in intervals when there are no products inside the detector head) rather than first calibrating the system at the range of operating frequencies and then adjusting the measured output signal to compensate for any imbalance and/or noise or delays in the system during testing phase of the products. In all cases, a database or look-up table is created showing the adjustments necessary to an adjustable balance signal and/or the reference signals for a range of operating frequencies. This can be stored internally in the processor of the metal detector, i.e. the internal memory of the computer or equally on separate hardware. Alternatively, data from the metal detector may be communicated to an external server and processor via the internet or telecommunication lines.

The invention claimed is:

1. A method of operation of a variable frequency metal detector having a driver circuit for establishing an alternating magnetic field in a coil system so as to generate an output signal at a given frequency, said driver circuit comprises a plurality of switches being arranged to cause the coil system to be driven at a frequency determined by the operation of the plurality of switches, the method comprising the steps of
   a. generating an adjustable balance signal;
   b. combining the adjustable balance signal with the output signal of the detector;
   c. varying the adjustable balance signal so as to provide a compensated signal;
   whereby the output signal and/or the adjustable balance signal is filtered to remove one or more harmonics.

2. A method as claimed in claim 1, wherein the driver circuit generates a drive signal for establishing an alternating magnetic field in a coil system and the adjustable balance signal is derived from the drive signal.

3. A method as claimed in claim 1, further comprising the method of measuring the compensated signal and if the compensated signal is above a predetermined threshold value, repeating step (c) so that when combined with the output signal of the detector provides the compensated signal.

4. A method as claimed in claim 3, where the predetermined threshold value is substantially equal to zero volts.

5. A method as claimed in claim 1, wherein the adjustable balance signal is incremented in sequential steps.

6. A method as claimed in claim 1, wherein the output signal of the detector has a phase component and a magnitude and the adjustable balance signal has a phase component and a magnitude and wherein the phase component and/or the magnitude of the output signal of the detector is combined with the phase component and/or the magnitude of adjustable balance signal to provide the compensated signal.

7. A method as claimed in claim 1, wherein the adjustments made to the adjustable balance signal at a given frequency is stored in a database or look-up table.

8. A method of calibrating a metal detection comprising the step of repeating the steps as defined in claim 1 for successive frequencies.

9. A method as claimed in claim 8, wherein the frequency is varied incrementally.

10. A method as claimed in claim 9, wherein the frequency is successively varied in substantially 10 Hz increments.

11. A method as claimed in claim 1, wherein the adjustable balance signal is varied by a potentiometer.

12. A method as claimed in claim 11, wherein the potentiometer is a first and second potentiometer.

13. A method as claimed in claim 12, wherein the adjustable balance signal has a first adjustable balance signal and a second adjustable balance signal, said first adjustable balance signal is varied by the first potentiometer and said second adjustable balance signal is varied by the second potentiometer.

14. A method as claimed claim 13, wherein the first adjustable balance signal is not in phase with the second adjustable balance signal.

15. A method as claimed in claim 14, wherein the first adjustable balance signal is in phase with the drive signal and the second adjustable balance signal is not in phase with the drive signal.

16. A method as claimed in claim 15, wherein the second adjustable signal is substantially 90° out of phase with the drive signal.

17. A method as claimed in claim 13, wherein the first adjustable signal is not in phase with the drive signal.

18. A metal detector for carrying the method steps as defined in claim 1 comprising:

a. a coil system;
b. a driver circuit for establishing an alternating magnetic field in the coil system to generate an output signal and an adjustable balance signal in the absence of an product at a given frequency;
c. an adjustor for varying the adjustable balance signal at said given frequency so as to combine with the output signal of the detector to provide a compensated signal.

19. A metal detector as claims in claim 18, wherein the adjuster comprises a potentiometer.

20. A metal detector as claimed in claim 18, comprising a microprocessor and an electronically programmable logic device for varying the adjustable balance signal at the given operational frequency and combining said adjustable balance signal with the output signal at said given operation frequency of the coil system to provide the compensated signal.

21. A metal detector as claimed in claim 18, wherein the driver is arranged to operate the coil system at any one of a selection of plurality of different frequencies.

22. A metal detector as claimed in claim 18, in which the driver comprises a plurality of switches being arranged to alternatively connect the coil system directly across a potential difference to cause the coil system to be driven at an operating frequency determined by the operation of the switches.

23. A metal detector as claimed in claim 22, wherein the driver circuit comprises a microprocessor and an electronically programmable logic device, the output of the electronically programmable logic device controls said switches, wherein for a particular detection coil, a plurality of drive maps are stored in the electronically programmable logic device or the microprocessor each containing a switching sequence for the switches for a respective predetermined frequency of operation of the metal detector, wherein the microprocessor selects an appropriate frequency depending on the selected frequency of operation.

24. A metal detector as claimed in claim 18, further comprising a low pass filter to filter one or more harmonics from the output signal and/or the adjustable balance signal.

25. A method of operation of a metal detector having a driver circuit for generating a drive signal for establishing an alternating magnetic field in a coil system so as to generate an output signal at a given frequency, said output signal having a first component and a second component, the first component being out of phase with respect to the second component at a predetermined phase angle, wherein the output signal is compensated for any noise or delay in measuring the output signal at a given frequency by the steps of:
a. measuring the output signal in the presence of ferrite between the coil system at a given frequency,
b. digitally adjusting the output signal so that the output signal in the first or second component of the output signal is equal to or below a first predetermined threshold value and the output signal in the second or first component of the output signal is above a second predetermined threshold value,
c. storing the adjustments made to the output signal at said given frequency in a database or a look-up table,
d. repeating steps a, b and c for different frequencies.

26. A method as claimed in claim 25, wherein the output signal is digitally adjusted so as to discriminate the output signal in the first or second component of the output signal such that the output signal in the first or second component of the output signal is substantially equal to zero.

27. A method as claimed in claim 26, wherein the first component of the output signal is substantially in phase quadrature with the second component of the output signal.

28. A method as claimed in claim 26, wherein the first predetermined threshold value is substantially zero.

29. A method as claimed in claim 1 wherein the metal detector comprises a phase sensitive detector, whereby the output signal is compensated for any noise or delay in measuring the output signal at a given frequency by the steps of;
a. generating a reference signal;
b. combining the reference signal with the output signal of ferrite in the phase sensitive detector at a given frequency
c. digitally adjusting the reference signal such that when combined with the output signal from ferrite, the output signal in the first or second component of the output signal is equal to or below a first predetermined threshold value and the output signal in the second or first component of the output signal is above or equal to a second predetermined threshold value;
d. storing the adjustments made to the reference signal in a database or look-up table;
e. repeating steps a, b, c and d at different frequencies.

30. A method as claimed in claim 29, wherein the metal detector comprises a first and second phase sensitive detector and the reference signal comprises a first reference signal and a second reference signal such that at a given frequency, the first reference signal is combined with the output signal in the first phase sensitive detector to produce a first component of the output signal and the second reference signal is combined with the output signal in the second phase sensitive detector to produce a second component of the output signal.

31. A method as claimed in claim 30, where the first reference signal is substantially in phase quadrature with the second reference signal.

32. A method as claimed in claim 29, wherein the reference signal at a given frequency is varied incrementally.

33. A method as claimed in claim 32, wherein the reference signal is incremented in sequential steps.

34. A method as claimed in claim 29, wherein the reference signal is adjusted by incorporating a delay factor in the reference signal.

35. A method as claimed in claim 29, wherein the phase and/or the magnitude of the reference signal is adjusted.

36. A method as claimed in claim 29, wherein the reference signal is based on the drive signal.

37. A method as claimed in claim 25, wherein said driver circuit comprises a plurality of switches being arranged to cause the coil system to be driven at a frequency determined by the operation of the plurality of switches.

38. A method for scanning a product to detect metal on, in or associated with that product as defined in claim 1; comprising the steps of;
a. retrieving the adjustments made to the output signal at a desired operational frequency of the metal detector from the database or look-up table;
b. digitally adjusting the output signal to the adjustments stored in the database or look-up table so to compensate for any noise or delay in measuring the output signal.

39. A method as claimed in claim 38, wherein the phase and/or magnitude of the output signal is compensated for the adjustments stored in the database or look-up table.

40. A metal detector for carrying the method steps as defined in claim 1 comprising:
a. a coil system;

b. a driver circuit for establishing an alternating magnetic field in the coil system so as to generate an output signal and a reference signal at a given frequency;

c. an adjustor for varying the reference signal at said given frequency so as to compensate for any noise or delay in measuring the output signal.

41. A metal detector as claimed in claim 40, comprising a microprocessor and an electronically programmable logic device for adjusting the reference signal and combining said reference signal with the output signal in the phase sensitive detector at said given operation frequency of the coil system so as to compensate for any noise or delay in measuring the output signal.

42. A metal detector as claimed in claim 40, wherein the driver is arranged to operate the coil system at any one of a selection of plurality of different frequencies.

43. A metal detector as claimed in claim 42, in which the driver comprises a plurality of switches being arranged to alternatively connect the coil system directly across a potential difference to cause the coil system to be driven at an operating frequency determined by the operation of the switches.

44. A metal detector as claimed in claim 43, wherein the driver circuit comprises a microprocessor and an electronically programmable logic device, the output of the electronically programmable logic device controls said switches, wherein for a particular detection coil, a plurality of drive maps are stored in the electronically programmable logic device or the microprocessor each containing a switching sequence for the switches for a respective predetermined frequency of operation of the metal detector, wherein the microprocessor selects an appropriate frequency depending on the selected frequency of operation.

45. A method as claimed in claim 1, wherein the method results in the balancing of the output signal.

46. A method as claimed in claim 45, wherein the step of combining the adjustable balance signal with the output signal of the detector produces a combined output signal.

47. A method as claimed in claim 46, wherein the output signal and the adjustable balance signal are individually filtered to remove one or more harmonics prior to being combined to form the combined output signal that is compensated.

48. A method of balancing an output signal of a variable frequency metal detector, said variable frequency metal detector comprising a driver circuit for establishing an alternating magnetic field in a coil system so as to generate an output signal at a given frequency, said driver circuit comprises a plurality of switches being arranged to cause the coil system to be driven at a frequency determined by the operation of the plurality switches, including the steps of;

a. generating an adjustable balance signal;

b. combining the adjustable balance signal with the output signal of the detector to produce a combined output signal;

c. varying the adjustable balance signal so as to compensate the combined output signal;

d. inputting the combined output signal that is compensated into a detection circuitry comprising phase sensitive detectors.

49. A method for scanning a product to detect metal on, in or associated with that product using a variable frequency metal detector having a driver circuit for establishing an alternating magnetic field at a given operational frequency in a coil system so as to generate an output signal comprising the step of:

a. balancing the output signal of the variable frequency metal detector;

b. selecting a desired operational frequency in the absence of the product;

c. retrieving the adjustments made to the adjustable balance signal at this desired frequency from the database;

d. adjusting the adjustable balance signal to the adjustments stored in the database;

e. compensating the output signal for the adjustable balance signal.

50. The method as claimed in claim 49, wherein the driver circuit generates a drive signal for establishing an alternating magnetic field in the coil system and the adjustable balance signal is derived from the drive signal.

51. The method as claimed in claim 50, wherein the adjustable balance signal is incremented in sequential steps.

52. The method of claim 51, wherein the output signal of the detector has a phase component and a magnitude and the adjustable balance signal has a phase component and a magnitude and wherein the phase component and/or the magnitude of the output signal of the detector is combined with the phase component and/or the magnitude of adjustable balance signal to compensate the combined output signal.

53. A method as claimed in claim 1, wherein the method of operation of a variable frequency metal detector is a method of balancing the output signal of the variable frequency metal detector, wherein the action of combining the adjustable balance signal with the output signal of the detector produces a combined output signal, the action of varying the adjustable balance signal so as to provide a compensated signal compensates the combined output signal, whereby the output signal and the adjustable balance signal are individually filtered to remove one or more harmonics prior to being combined to form the combined output signal that is compensated.

54. A method as claimed in claim 48, wherein the combined output signal that is compensated is filtered to remove one or more harmonics prior to being input into the detection circuitry.

* * * * *